(12) United States Patent
Har-Shai

(10) Patent No.: US 9,409,698 B2
(45) Date of Patent: Aug. 9, 2016

(54) PROPELLANT-FREE PRESSURIZED MATERIAL DISPENSER

(75) Inventor: Gadi Har-Shai, Hod-HaSharon (IL)

(73) Assignee: GreenSpense Ltd., Misgav (IL)

( * ) Notice: Subject to any disclaimer, the term of this patent is extended or adjusted under 35 U.S.C. 154(b) by 0 days.

(21) Appl. No.: 14/002,774

(22) PCT Filed: Mar. 1, 2012

(86) PCT No.: PCT/IL2012/050063
§ 371 (c)(1),
(2), (4) Date: Sep. 3, 2013

(87) PCT Pub. No.: WO2012/117401
PCT Pub. Date: Sep. 7, 2012

(65) Prior Publication Data
US 2013/0345647 A1 Dec. 26, 2013

Related U.S. Application Data

(60) Provisional application No. 61/448,271, filed on Mar. 2, 2011.

(51) Int. Cl.
*B65D 83/00* (2006.01)
*A62C 13/00* (2006.01)
*A61M 5/148* (2006.01)

(52) U.S. Cl.
CPC ........... *B65D 83/0061* (2013.01); *A61M 5/148* (2013.01); *A62C 13/00* (2013.01); *Y10T 29/49826* (2015.01)

(58) Field of Classification Search
USPC ............ 222/94, 95, 105, 107, 211, 212, 215, 222/386.5, 387, 394
See application file for complete search history.

(56) References Cited

U.S. PATENT DOCUMENTS

| 2,966,282 | A | 12/1960 | Geisler |
| 3,791,557 | A | 2/1974 | Venus, Jr. |
| 3,981,415 | A | 9/1976 | Fowler et al. |
| 4,077,543 | A | 3/1978 | Kulikowski et al. |
| 4,121,737 | A | 10/1978 | Kain |
| 4,222,499 | A | 9/1980 | Lee et al. |
| 4,251,032 | A | 2/1981 | Werding |

(Continued)

FOREIGN PATENT DOCUMENTS

| CN | 101058650 | 10/2007 |
| CN | 101735493 | 6/2010 |

(Continued)

OTHER PUBLICATIONS

International Search Report and the Written Opinion Dated Jul. 30, 2012 From the International Searching Authority Re. Application No. PCT/IL2012/050063.

Das et al. "Nanocomposite Based on Chloroprene Rubber: Effect of Chemical Nature and Organic Modification of Nanoclay on the Vulcanizate Properties", European Polymer Journal, XP025628032, 44(11): 3456-3465, Nov. 1, 2008.

Kim et al. "Fabrication of Aligned Carbon Nanotube-Filled Rubber Composite", Scripta Materialia, XP002678869, 54: 31-35, 2006.

International Preliminary Report on Patentability Dated Sep. 12, 2013 From the International Bureau of WIPO Re. Application No. PCT/IL2012/050063.

International Search Report and the Written Opinion Dated Dec. 20, 2012 From the International Searching Authority Re. Application No. PCT/IL2012/050360.

Schwartz "Nanocomposites for Advanced Elastomers", The 4th International Conference on Nanotechnology for the Plastics & Rubber Industries, Ramat Gan, Israel, Feb. 2, 2009, 37 P., Feb. 2009.

International Search Report and the Written Opinion Dated Jun. 23, 2014 From the International Searching Authority Re. Application No. PCT/IL2014/050060.

(Continued)

*Primary Examiner* — Paul R Durand
*Assistant Examiner* — Vishal Pancholi

(57) ABSTRACT

Devices and methods for dispensing a fluidly dispensable material under pressure but without using a gas propellant are presented. In some embodiments an elastic sleeve is utilized to impart pressure to a bag of dispensable material positioned within the sleeve. Pressure so created pressurizes contents of the bag, which can then be dispensed through a valve. Methods for manufacturing various embodiments are presented.

25 Claims, 20 Drawing Sheets

(56) References Cited

U.S. PATENT DOCUMENTS

| | | | |
|---|---|---|---|
| 4,458,830 A * | 7/1984 | Werding | 222/131 |
| 4,574,746 A | 3/1986 | Keyes, IV et al. | |
| 4,964,540 A | 10/1990 | Katz | |
| 4,981,238 A | 1/1991 | Wenmaekers | |
| 5,014,881 A * | 5/1991 | Andris | 222/207 |
| 5,060,700 A | 10/1991 | Wenmaekers | |
| 5,080,652 A * | 1/1992 | Sancoff et al. | 604/132 |
| 5,111,971 A | 5/1992 | Winer | |
| 5,127,554 A | 7/1992 | Loychuk | |
| 5,303,853 A | 4/1994 | Nye | |
| 5,526,957 A * | 6/1996 | Brown et al. | 222/94 |
| 5,927,551 A | 7/1999 | Taylor et al. | |
| 6,407,155 B1 | 6/2002 | Qian et al. | |
| 6,413,239 B1 | 7/2002 | Burns et al. | |
| 6,818,693 B2 | 11/2004 | Heinrich et al. | |
| 2005/0027058 A1 | 2/2005 | Dias et al. | |
| 2006/0243741 A1 | 11/2006 | Schiefer | |
| 2007/0267437 A1 | 11/2007 | Nimmo et al. | |
| 2008/0272145 A1 | 11/2008 | Nimmo et al. | |
| 2009/0045222 A1 | 2/2009 | Nimmo et al. | |
| 2009/0047969 A1 | 2/2009 | Lee et al. | |
| 2010/0133295 A1 * | 6/2010 | Chan et al. | 222/95 |
| 2011/0060086 A1 | 3/2011 | Rodgers et al. | |
| 2011/0108574 A1 | 5/2011 | Nimmo et al. | |
| 2011/0130507 A1 | 6/2011 | Leu et al. | |
| 2012/0004347 A1 | 1/2012 | Ratnayake et al. | |
| 2012/0097706 A1 | 4/2012 | Nimmo et al. | |
| 2013/0072607 A1 | 3/2013 | Schwartz | |
| 2014/0031468 A1 | 1/2014 | Schwartz | |
| 2015/0307258 A1 | 10/2015 | Har-Shai et al. | |
| 2015/0368438 A1 | 12/2015 | Schwartz et al. | |

FOREIGN PATENT DOCUMENTS

| | | |
|---|---|---|
| CN | 102504361 | 6/2012 |
| DE | 4333627 | 4/1995 |
| DE | 102004028734 | 12/2005 |
| DE | 102010018890 | 11/2011 |
| EP | 0248755 | 12/1987 |
| EP | 0300886 | 1/1989 |
| EP | 0324289 | 7/1989 |
| EP | 0178573 | 2/1992 |
| EP | 1026102 | 8/2000 |
| EP | 1851135 | 7/2008 |
| EP | 1984279 | 11/2009 |
| EP | 2188191 | 6/2011 |
| EP | 2129598 | 4/2012 |
| EP | 2188962 | 10/2012 |
| EP | 2509267 | 10/2012 |
| EP | 2597834 | 5/2013 |
| FR | 2242158 | 3/1975 |
| FR | 2608137 | 6/1988 |
| FR | 2707264 | 1/1995 |
| GB | 1463336 | 2/1977 |
| GB | 2209056 | 4/1989 |
| GB | 2262312 | 6/1993 |
| GB | 2278823 | 12/1994 |
| WO | WO 88/00563 | 1/1988 |
| WO | WO 95/09784 | 4/1995 |
| WO | WO 01/15583 | 3/2001 |
| WO | WO 03/022711 | 3/2003 |
| WO | WO 2004/080841 | 9/2004 |
| WO | WO 2005/113660 | 12/2005 |
| WO | WO 2007/093889 | 8/2007 |
| WO | WO 2010/085979 | 8/2010 |
| WO | WO 2010/145677 | 12/2010 |
| WO | WO 2011/139545 | 11/2011 |
| WO | WO 2012/117401 | 9/2012 |
| WO | WO 2013/008241 | 1/2013 |
| WO | WO 2014/111939 | 7/2014 |
| WO | WO 2014/111940 | 7/2014 |

OTHER PUBLICATIONS

Huang et al. CN 101735493, Database WPI [Online], Thomson Scientific, XP002725326, Week 201050, Database Accession No. 2010-J38836, 2010. Abstract.
Lv et al. CN 102504361, Database WPI [Online], Thomson Scientific, XP002725327, Week 201253, Database Accession No. 2012-J53639, 2012. Abstract.
Zhang CN101058650, Database WPI [Online], Thomson Scientific, XP002725328, Week 200822, Database Accession No. 2008-D03393, 2008. Abstract.
Restriction Official Action Dated Sep. 4, 2014 From the US Patent and Trademark Office Re. U.S. Appl. No. 13/949,456.
Official Action Dated May 24, 2013 From the US Patent and Trademark Office Re. U.S. Appl. No. 13/546,228.
Ansarifar et al. "Optimising the Chemical Bonding Between Silanised Silica Nanofiller and Natural Rubber and Assessing Its Effects on the Properties of the Rubber", International Journal of Adhesion and Adhesives, 26(6): 454-463, Sep. 2006. Abstract.
Bai et al. "Reinforcement of Hydrogenated Carboxylated Nitrile-Butadiene Rubber With Exfoliated Graphene Oxide", Carbon, 49: 1608-1613, 2011.
Das et al. "Reinforcement and Migration of Nanoclay in Polychloroprene/Ethylene-Propylene-Diene-Monomer Rubber Blends", Composites Science and Technology, 71: 276-281, 2011.
Kim et al. "Effect of Metal Compounds on Thermal Degradation Behavior of Aliphatic Poly(Hydroxyalkanoic Acid)s," Polymer Degradation and Stability, 93(4): 776-785, 2008.
Koo "Closite Additives," Polymer Nanocomposites: Processing, Characterization, and Applications, Chapter 2: pp. 16-19. McGraw-Hill: New York, New York (2006).
Struktol "Struktol® TS 30, Struktol® TS 30-DL, Struktol® TS 35, Struktol® TS 35-DL. Tackifiers and Softeners", Technical Data Sheet, Schill + Seilacher Struktol Company of America, 1 P., 2004.
Communication Relating to the Results of the Partial International Search Dated Jun. 4, 2014 From the International Searching Authority Re. Application No. PCT/IL2014/050059.
Official Action Dated Nov. 14, 2014 From the US Patent and Trademark Office Re. U.S. Appl. No. 13/949,456.
Bhattacharya et al. "Tailoring Properties of Styrene Butadiene Rubber Nanocomposite by Various Nanofillers and Their Dispersion", Polymer Engineering and Science, 49(1): 81-98, Jan. 2009.
Communication Pursuant to Article 94(3) EPC Dated Jan. 7, 2015 From the European Patent Office Re. Application No. 12714383.2.
Official Action Dated Jun. 12, 2015 From the US Patent and Trademark Office Re. U.S. Appl. No. 13/949,456.
Kim et al. "SBR/Organoclay Nanocomposites for the Application on Tire Tread Compounds" Macromolcular Research. 17(10): 776-784, 2009.
International Search Report and the Written Opinion Dated Sep. 30, 2014 From the International Searching Authority Re. Application No. PCT/IL2014/050059.
Communication Pursuant to Article 94(3) EPC Dated Sep. 24, 2015 From the European Patent Office Re. Application No. 12714383.2.
Advisory Action Before the Filing of an Appeal Brief Dated Nov. 20, 2015 From the US Patent and Trademark Office Re. U.S. Appl. No. 13/949,456.
Office Action Dated Jan. 11, 2016 From the Israel Patent Office Re. Application No. 220867 and Its Translation Into English.
Official Action Dated Dec. 31, 2015 From the US Patent and Trademark Office Re. U.S. Appl. No. 13/949,456.
International Preliminary Report on Patentability Dated Jul. 30, 2015 From the International Bureau of WIPO Re. Application No. PCT/IL2014/050059.
International Preliminary Report on Patentability Dated Jul. 30, 2015 From the International Bureau of WIPO Re. Application No. PCT/IL2014/050060.

* cited by examiner

PROPELLANT-FREE PRESSURIZED MATERIAL DISPENSER

RELATED APPLICATIONS

This application is a National Phase of PCT Patent Application No. PCT/IL2012/050063 having International filing date of Mar. 1, 2012, which claims the benefit of priority under 35 USC §119(e) of U.S. Provisional Patent Application No. 61/448,271 filed Mar. 2, 2011. The contents of the above applications are incorporated herein by reference in their entirety.

FIELD AND BACKGROUND OF THE INVENTION

The present invention, in some embodiments thereof, relates to a materials dispenser and, more particularly, but not exclusively, to devices for dispensing liquids, pastes, foams, and the like, under pressure.

Aerosol spray cans are known throughout modern society, and are used in myriad products found in food stores, pharmacies, tool shops, and more. Fire extinguishers also provide a stream of material under pressure.

Aerosol canisters typically deliver material pressurized to seven or eight bars. A few methods are popular. Single Compartment methods mix a deliverable material with a propellant (a compressed gas), and spray both through a valve. Dual Compartment methods separate the deliverable material from the propellant to avoid interaction between them, to increase shelf life of the product, and for various other reasons. Some Dual Compartment methods use a bag for deliverable material. Some separate material from propellant using a piston barrier. In both cases a compartment with a pressurized propellant is used to pressurize a compartment with a deliverable material, which can then be delivered under pressure through a valve. Practical considerations and in some jurisdictions also laws and regulations require that containers for aerosol products using a propellant (typically compressed to 7-8 bars) to be cylindrical in format, for safety reasons. Containers are also required to be metal or of thick glass or of rigid plastic, or in any case to be of sufficient strength and thickness to safely withstand this pressure. If made of metal other than aluminum (which is relatively expensive), containers are usually made out of TinPlate and coated with lacquers or other coatings to prevent them from rusting and releasing the pressure in unintended ways. As a result, aerosol containers are often relatively expensive to make, to transport, and to handle in bulk, are constrained to be in a standard shape, and are difficult to dispose of in an ecologically desirable manner.

For low pressure dispensing applications, the state of the art is generally that users use manual pressure to pump or squeeze products from containers, for example to get food and suntan lotion out of plastic squeeze bottles, or to get toothpaste and pharmaceuticals out of collapsible tubes, or press on a mechanical pump to deliver the product. In addition to the potential inconvenience attached to the use of many such packages, they suffer from the additional potential disadvantage that air entering such packages interacts with the material therein, reducing shelf life. An additional possible disadvantage is that it is often difficult or impossible to empty them completely, leading to either a messy operation or wastage of products, frustration of users, and/or unnecessary expense.

The following patent documents may be relevant to this field.

U.S. Pat. No. 4,121,737: Apparatus for pressure dispensing of fluids
WO9509784: Package as dispenser for a pressurized fluid substance
U.S. Pat. No. 4,222,499: Pressurized fluid dispensing apparatus having expansible bladder held in place with compressive forces
DE102004028734: Environmentally friendly aerosol especially for cosmetic applications has the contents held in an elastic inner liner which contracts to expel the charge without any pump or propellant
U.S. Pat. No. 5,127,554: Aerosol power system
WO2004080841: Spray device
U.S. Pat. No. 2,966,282: Dispensing package for fluids
GB2209056: Liquid container
WO0115583: Food Container
U.S. Pat. No. 3,981,415: Dispenser with expansible member and contracting fabric
EP0248755: Pressurized container
FR2608137: Device in the form of a container of fluid or powder packaged under pressure to facilitate its self-ejection or controlled self-outflow
US2009045222: Bag of variable volume, device suitable for dispensing fluids
US2006243741: Aerosol can
GB2278823: Liner for dispensing container
U.S. Pat. No. 4,077,543: Propellantless aerosol container
FR2707264(A1): Device for dispensing a substance and system adapted for filling the latter
U.S. Pat. No. 3,791,557: Non-aerosol container with expansible bladder and expelling force providing sheath
U.S. Pat. No. 5,111,971(A): Self-pressurized container having a convoluted liner and an elastomeric sleeve
U.S. Pat. No. 4,251,032: Appliance for discharging gaseous, liquid or pasty product, and process of its manufacture
U.S. Pat. No. 5,927,551: Power assembly apparatus
U.S. Pat. No. 4,964,540: Pressurized fluid dispenser and method of making the same
U.S. Pat. No. 5,060,700: Dispenser for a viscous substance
U.S. Pat. No. 4,981,238: Dispensing can for viscous substances
WO/2010/145677
WO/2010/085979

SUMMARY OF THE INVENTION

The present invention, in some embodiments thereof, relates to methods and devices for dispensing a material under pressure.

In some embodiments an elastic sleeve used to compress a bag comprising or connected to a valve. The bag is filled or partially filled with a liquid or paste or foam or mixture or other fluidly deliverable substance, or a powder, which is the material to be dispensed. Pressure from the sleeve pressurizes material in the bag, which consequently flows out of the bag under pressure when the valve is opened.

According to an aspect of some embodiments of the present invention there is provided a device for dispensing a material under pressure, comprising a) a flexible bag for containing the material and a valve positioned at a first extremity of the bag and operable to control exit of the material from the bag; and
b) an elastic sleeve which comprises a lumen, the sleeve being fitted over the bag and containing the bag within the lumen;

the sleeve and the bag being sized and positioned so that elastic contraction forces in the sleeve exerts compressive pressure on the bag when the bag is at least partially filled with the material.

According to some embodiments of the invention, the sleeve comprises the and first and second open ends.

According to some embodiments of the invention, the elastic contraction forces in the sleeve exert compressive pressure on the bag when the bag is substantially empty of the material.

According to some embodiments of the invention, the pressure on the bag when the bag is empty is between 1.05 bar and 4 bar.

According to some embodiments of the invention, the ratio of pressure on the bag when the bag is full to pressure on the bag when the bag is empty is greater than 2/1 and less than 4.5/1.

According to some embodiments of the invention, the bag is comprised within a Bag-on valve assembly.

According to some embodiments of the invention, the bag is adapted for Bag-in can assembly.

According to some embodiments of the invention, the sleeve is constructed of a material which comprises nano-particles.

According to some embodiments of the invention, the nano-particles comprise a clay.

According to some embodiments of the invention, the nano-particles are selected from at least one of a group comprising Nanoclay, Nanosilica, Graphene, and CarbonNanotubes.

According to some embodiments of the invention, the valve is held by a valve assembly structure, and the first open end of the sleeve surrounds a portion of the valve assembly structure and compressive forces exerted by the sleeve on the valve assembly structure anchor the first open end of the sleeve to the valve assembly structure.

According to some embodiments of the invention, the pressure exerted by the sleeve on the bag is at least 2 bar when the bag is empty and at least 6 bar when the bag is full.

According to some embodiments of the invention, the sleeve is of consistent profile along its length.

According to some embodiments of the invention, the sleeve is cut from an extruded tube.

According to some embodiments of the invention, the tube comprises a plurality of layers at least some of which have differing physical characteristics.

According to some embodiments of the invention, the tube comprises a plurality of longitudinal strips at least some of which have differing physical characteristics.

According to some embodiments of the invention, the second open end of the sleeve extends beyond the bag when the first open end of the sleeve is positioned around the valve assembly structure.

According to some embodiments of the invention, the device further comprises an external container which contains the bag and the sleeve.

According to some embodiments of the invention, the external container is airtight.

According to some embodiments of the invention, the external container is sealed in a manner not designed to maintain a pressure differential between contents of the container and room pressure outside the container.

According to some embodiments of the invention, the device further comprises an external container which contains the bag and the sleeve, and wherein the first end of the sleeve is near the valve and the second end of the sleeve is supported by a bottom of the external container.

According to some embodiments of the invention, the device further comprises an external container which contains the bag and the sleeve, and wherein a bottom of the bag is supported by a bottom of the external container.

According to some embodiments of the invention, the external container is non-cylindrical.

According to some embodiments of the invention, the external container is cannot hold a pressure above 2 bar.

According to some embodiments of the invention, the external container attaches to the bag and sleeve combination by means of an attachment which comprises one of
  a) a screw thread;
  b) a locking snap mechanism;
  c) a glue; and
  d) a weld.

According to some embodiments of the invention, the sleeve is extruded in at least first and second layers, and the first layer forms the outer external surface of the sleeve, and presents aesthetic properties which differ from those of the second layer.

According to some embodiments of the invention, the sleeve comprises at least first and second layers, and the first layer forms a surface of the lumen of the sleeve, and has at least one of
  a) Permeability lower than that of the second layer; and
  b) Reactivity lower than that of the second layer.

According to some embodiments of the invention, the sleeve comprises at least first and second layers, and the first layer has different elastic properties than the second layer.

According to some embodiments of the invention, the sleeve comprises a metallic spring.

According to some embodiments of the invention, the sleeve comprises an elastic band.

According to some embodiments of the invention, a wall of the sleeve is less than 3 mm in thickness, and wherein the sleeve exerts a pressure of at least 7 bar on the bag.

According to some embodiments of the invention, the device further comprises surfaces which support portions of the bag which are not in contact with the sleeve, when the bag is filled.

According to some embodiments of the invention, the material is a food.

According to some embodiments of the invention, the device the material is a cosmetic product.

According to some embodiments of the invention, the device the material is selected from a group consisting of a paint, a lacquer, a glue, a lubricant, a sealant and a paste.

According to some embodiments of the invention, the device the material is a selected from a group consisting of a personal care gel, a soap, a shampoo, and a sun care product.

According to some embodiments of the invention, the device the material is a toothpaste.

According to some embodiments of the invention, the device the material is selected from a group consisting of a cleaner, a polish, and an insecticide.

According to some embodiments of the invention, the material is a medication.

According to some embodiments of the invention, the material is effective in extinguishing fires.

According to some embodiments of the invention, the compressive pressure is above 9 bar.

According to some embodiments of the invention, the bag and sleeve combination is less than one inch in diameter.

According to an aspect of some embodiments of the present invention there is provided a method for creating a pressurized dispenser for a fluidly dispensable material, comprising a) providing an elastic sleeve with open first and second ends and a lumen extending from end to end;
b) causing the sleeve to expand elastically in a manner which increases diameter of the lumen;
c) inserting a flexible bag into the lumen while the lumen is expanded;
d) relaxing the elastic expansion of the sleeve; and
e) filling the bag with the material through a valve attached to the bag.

According to an aspect of some embodiments of the present invention there is provided a method for creating a pressurized dispenser for a fluidly dispensable material, comprising
a) providing an elastic sleeve with open first and second ends and a lumen extending from end to end;
b) filling a flexible bag with the material;
c) causing the sleeve to expand elastically in a manner which increases diameter of the lumen;
d) inserting the filled bag into the expanded sleeve;
e) relaxing the elastic expansion of the sleeve so that it contracts onto and pressurizes the bag and its contents.

According to some embodiments of the invention, the sleeve comprises a plurality of externally graspable shapes and the method further comprises expanding the sleeve by grasping the graspable shapes and pulling the shapes away from each other.

According to some embodiments of the invention, the device the method further comprises expanding the sleeve by inserting a plurality of objects into the lumen and then moving the objects away from each other, thereby expanding the lumen.

According to some embodiments of the invention, the device the method of expansion of the sleeve comprises using a pressure differential to expand the sleeve.

According to some embodiments of the invention, the method comprises inserting bag and sleeve into an opening in a standard aerosol can top, prior to filling the bag with the material through a valve attached to the bag.

According to some embodiments of the invention, the method comprises providing the elastic sleeve with open first and second ends and a lumen extending from end to end, by cutting the sleeve from a continuous roll of extruded sleeve material according to a user-selected length specification.

According to an aspect of some embodiments of the present invention there is provided a method for constructing pressurized dispensers of fluidly dispensable materials, comprising;
a) using a mechanical tool to forcibly expand an elastic sleeve;
b) inserting in the expanded sleeve a flexible bag which connects to a valve; and
c) filling the bag with the material.

According to some embodiments of the invention, the method comprises filling the bag through the valve while the elastic sleeve is exerting compressive pressure on the bag.

According to some embodiments of the invention, the method comprises filling the bag prior to inserting the bag in the sleeve.

According to some embodiments of the invention, the flexible bag is comprised in a Bag-on-valve module.

According to some embodiments of the invention, the method further comprises inserting an open first end of the sleeve around a valve assembly structure containing a valve of the Bag-on-valve module while the sleeve is expanded, and allowing the sleeve to contract around the valve assembly structure so that compression forces exerted by sleeve serve to fix the valve assembly structure within the sleeve end.

According to an aspect of some embodiments of the present invention there is provided an aerosol device comprising an elastic sleeve which exerts pressure on a flexible bag equipped with a valve.

According to an aspect of some embodiments of the present invention there is provided a device for dispensing a fluidly dispensable material at a pressure of less than 4.5 bar.

According to some embodiments of the invention, the device does not comprise a propellant gas.

According to an aspect of some embodiments of the present invention there is provided a transfusion device operable to supply a liquid for transfusion into the bloodstream of a patient, and which operates in any orientation independent of gravity.

According to some embodiments of the invention, the device comprises a bag containing the liquid, and an elastic sleeve compressing the bag.

According to an aspect of some embodiments of the present invention there is provided a method for modifying a production line for aerosol products to produce aerosol products without gas propellants, comprising
a) providing equipment which encloses bags for containing a dispensable material with a constricting sleeve which compresses the bags to aerosol pressures;
b) modifying product assembly equipment to insert the sleeve-enclosed bags instead of bags without sleeves in an aerosol product's external container; and
c) modifying the product assembly equipment so that it does not introduce a propellant into the external container.

According to some embodiments of the invention, the method further comprises filling the bags with the dispensable material before the bags are enclosed in the sleeve.

According to some embodiments of the invention, the method further comprises filling the bags with the dispensable material after the bags are enclosed in the sleeve.

According to an aspect of some embodiments of the present invention there is provided a method for producing a product which dispenses a material under pressure, comprising
a) providing a bag for holding the material connected to a valve for controlling passage of the material from the bag;
b) enclosing the bag in a sleeve which compresses the bag;
c) filling the bag with the material, thereby causing expansion of the sleeve and pressurizing the material.

According to some embodiments of the invention, the method further comprises inserting the bag enclosed in the sleeve in an external container, and subsequently filling the bag with the material under pressure through the valve.

According to an aspect of some embodiments of the present invention there is provided a method for producing a product which dispenses a material under pressure, comprising
a) providing a bag for holding the material;
b) filling the bag with the material;
c) closing the bag with a cap which comprises a valve for controlling passage of the material out of the bag;
d) enclosing the bag in a sleeve which compresses the bag, thereby pressurizing the material; and
e) inserting bag, material, and sleeve in an external container.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
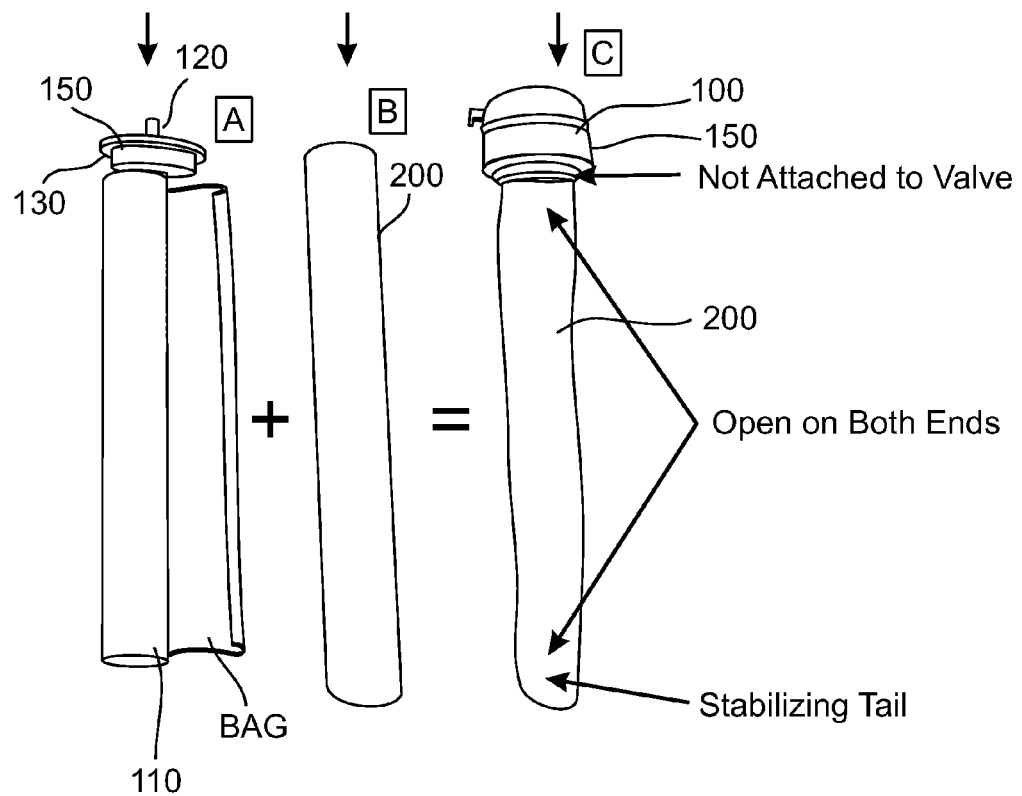
FIGS. 1 and 2 are based on photographs of an exemplary embodiment for dispensing materials under pressure, according to an embodiment of the present invention.

The present invention, in some embodiments thereof, relates to a materials dispenser and, more particularly, but not exclusively, to devices for dispensing a fluidly deliverable material, under pressure.

Overview:

In some embodiments a liquid or paste or foam or powder or mixture or other fluidly deliverable substance is dispensed under pressure provided by an elastic sleeve used to compress a bag comprising or connected to a valve, which bag contains the material to be dispensed. Compressive pressure from the sleeve pressurizes material in the bag, which consequently flows out of the bag under pressure when the valve is opened.

Some embodiments are aerosol dispensers and provide an alternative to prior art aerosol containers by providing a propellant-free device which stores contents at pressures appropriate for aerosol, and dispenses them through a valve. Some embodiments do not require tough, metallic, cylindrical containers: the bag+sleeve combination, which may optionally be placed within an external container for distribution and sale, does not subject that container to pressure. In some aerosol embodiments compressive pressure generated by the device is greater than 6 bar when the device is full (for example between 6.5 and 9 bar, for example between 7 and 8.5 bar), and is less than 5 bar (e.g. between 2-4 bar) when the device is empty.

Some embodiments provide a felicitous means for dispensing food, cosmetics, creams, ointments, medicines, IV transfusion materials, and other materials, under low pressure (e.g. slightly above ambient atmospheric pressure, or between 1-2 bar, 2-3 bar or 2-4.5 or 2-6 bar), and/or at low delivery rates.

It is anticipated that embodiments comprising a bag+sleeve combination will open up markets for, inter alia:
- self-dispensing food containers (e.g. for mayonnaise, ketchup, mustard, sauces, desserts, spreads, oil, pastry components),
- containers for cosmetics such as creams and lotions, skin care products and hair gels,
- industrial/technical applications such as paints, lacquers, glues, grease and other lubricants, sealants, pastes and other viscous materials,
- personal care products such as shaving, shower and shampooing gels, toothpaste, liquid soap and shampoo, sun care products,
- household products such as polishes and glass, bathroom and furniture and other cleaners, insecticides, air fresheners, and for plant irrigation,
- pharmaceutical and medical products such as medications (including dosage packages) and ointments, oral and nasal sprays, intravenous and intra-arterial transfusion of blood and/or fluids.

All the above are considered to be within the scope of the invention, however the above list is not to be considered limiting.

Some embodiments provide pressures of between 8-20 bar, useful for example in fire extinguishers and other specialized devices.

Some embodiments of the invention provide devices for dispensing material under pressure which are simpler and cheaper to make, lighter, require less expensive components, enable greater variety of shapes and sizes, can be adapted to a greater range of products, and are more ecologically sound than prior art devices.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention, in some embodiments thereof, relates to methods and devices for dispensing a material under pressure.

In some embodiments a section of an extruded rubber-based sleeve is used. Other mechanisms for producing compressive (i.e. centripetal) pressure on a bag contained within a compressing device are presented herein, and all sleeves and all such other mechanisms are included in the term "sleeve" as used herein.

For simplicity of exposition, in some cases, reference is made to the "top" and "bottom" of a dispensing device or a component thereof. As used herein, "top" refers to a portion of a device near the valve of the device, and "bottom" refers to the opposite end of the device, so that the "top" and "bottom" of the device are defined with respect to the device structure without reference to the device's temporary position in space.

In some embodiments the bag and valve are comprised in a "Bag-on-valve" (herein "BOV") module, a module well known in the art and used in many Dual Compartment aerosol product dispensers. In some embodiments, the well-known "Bag-in-can" (herein "BIC") structure is used.

Figure 2:
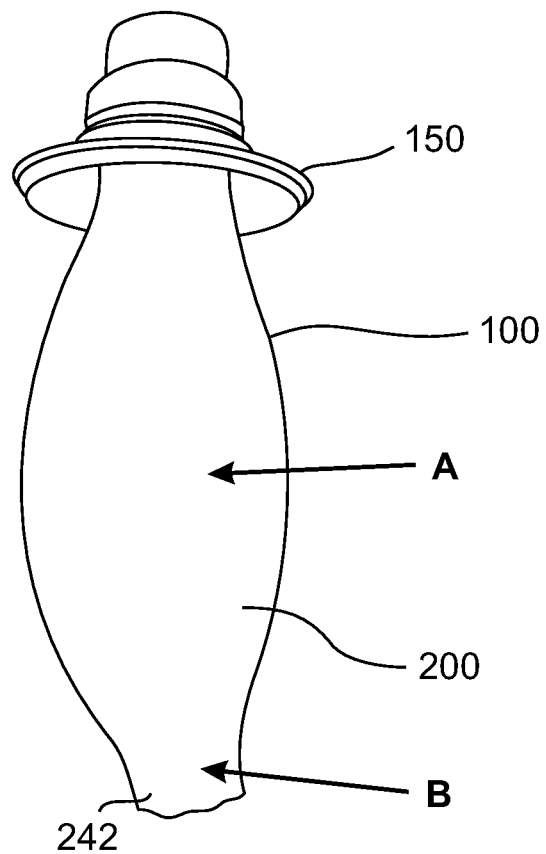

Exemplary Sleeve/Bag Module for Pressurizing Dispensable Materials:

Referring now to the drawings, FIGS. 1 and 2 are photographs of an exemplary embodiment, a pressure dispenser 100 (also called a "delivery module 100" herein) for dispensing fluidly dispensable materials under pressure, according to an embodiment of the present invention. In some embodiments discussed below, dispenser 100 placed within and connected to an external container. In other embodiments discussed below, dispenser 100 may be provided with only a cosmetic external layer. In some embodiments dispenser 100 may be sold and used without any external covering.

FIG. 1 presents at position 'A' a flexible bag 110 attached to a valve 120. Bag 110 is a bag or pouch capable of holding a material to be dispensed, and capable of being connected to a valve. Bag 110 will generally be constructed of a substance not expected to interact chemically with whatever material it is expected to hold and to dispense.

In the exemplary embodiment shown in the figure, bag 110 is shown as a Bag-on-valve combination ("BOV" herein), here labeled BOV 150. BOV 150 is a standard component of aerosol products and is well known in the industry.

A BOV 150 shown in the figure comprises a valve 120 and a valve assembly structure 130 which holds valve 120 and attaches it to bag 110. As shown in the figure, bag 110 is empty and partially rolled upon itself below valve 120. BOV valves generally comprise a spring holding the valve closed. When these valves are pressed against the spring a pathway is opened, enabling pressurized material to flow past the valve. However it is to be understood that other valves known in the art may be used.

Figure 3:
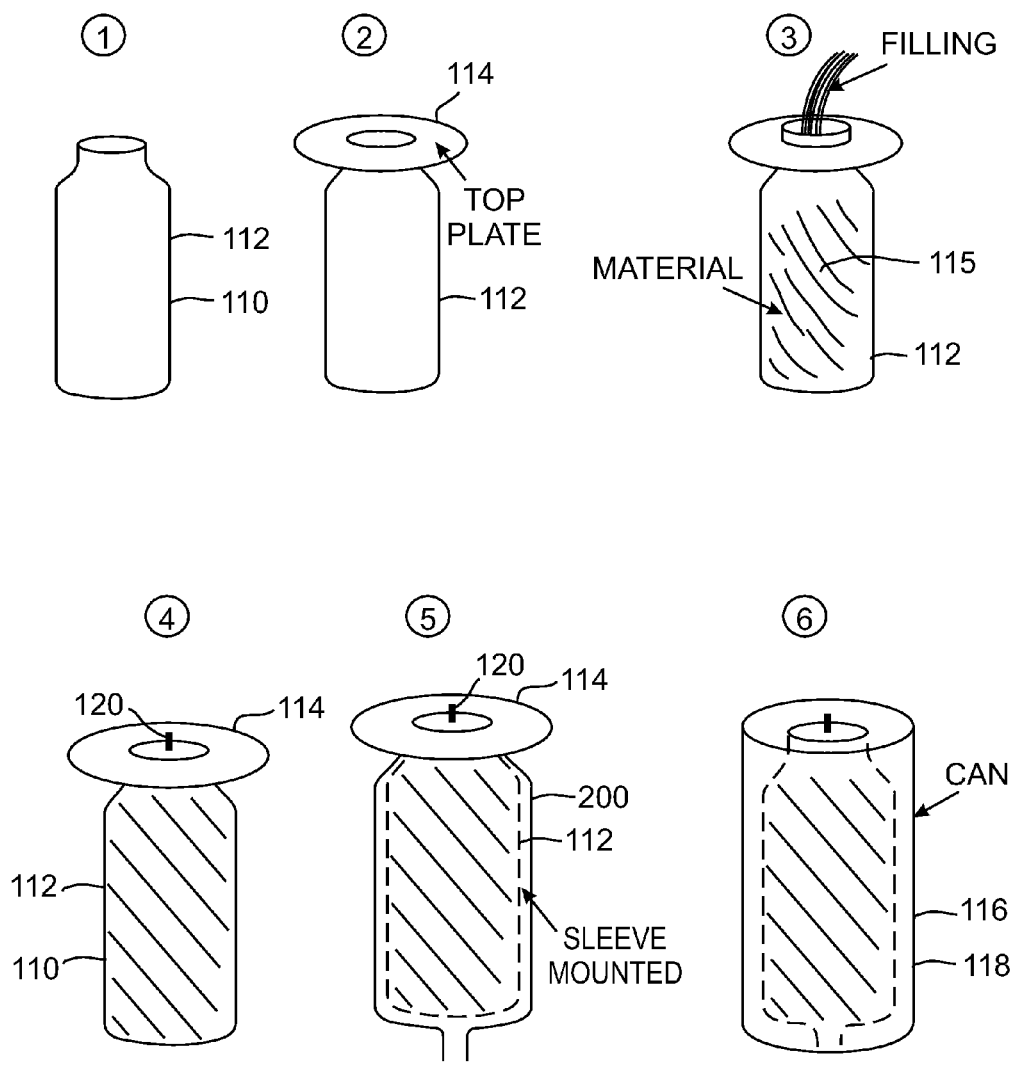
FIG. 3 is a simplified schematic of an alternative filling scheme, according to an embodiment of the invention.

At position 'B' in FIG. 1 an elastic sleeve 200 is presented. In the exemplary embodiment shown in FIG. 1 a cut section of a continuously extruded rubber-based tube is used as sleeve 200. However, the example of sleeve 200 shown in the figure should be considered exemplary and not limiting. Sleeve 200 is not necessarily extruded and not necessarily cut from a longer tube of similar material. Some additional optional constructions of sleeve 110 are shown in FIGS. 2 and 3. In general, sleeve 200 is characterized being sized and shaped to be able to contain bag 110 and to exert pressure on bag 110 when bag 110 is filled with material to be dispensed. In various embodiments discussed in detail below sleeve 200 is open on top and bottom, yet in some optional embodiments sleeve 200 is closed at the bottom. Optionally, sleeve 200 may be of non-uniform thickness or have a non-uniform distribution of other physical characteristics. For example, in some optional embodiments a sleeve 200 might be thinner near the ends, where less force is required.

At position 'C' in FIG. 1, sleeve 200 is shown enclosing bag 110, thereby forming a pressure dispensing module 100. According to manufacturing processes discussed below, bag 110, before or after being inserted into sleeve 200, may be filled with a dispensable material. Once bag 110 is filled and sleeve 200 is in place, sleeve 200 exerts a centripetal pressure on bag 110 by virtue of its elasticity. In some embodiments sleeve 200 exerts centripetal pressure on bag 110 even when bag 110 is empty, and sleeve 200 must be stretched to some degree in order for bag 110 to be inserted therein.

FIG. 2 shows dispensing module 100 after bag 110 has been filled with a material to be dispensed. In some embodiments bag 110 is filled through valve 110, dispensable material being optionally forced under pressure into bag 110 after bag 110 is positioned within sleeve 200. As may be seen in the figure, sleeve 200 is stretched to give place to material contents which have been inserted in bag 110, and which are being held under pressure, with bag 110 holding the contents and sleeve 200 applying the pressure. FIG. 2 is an example of a BOV implementation shown without a container so as to make visible the shape of sleeve 200 when a BOV bag within is filled. In some embodiments and in normal use, assembly of a BOV aerosol comprises placing the BOV bag within a sleeve 200 (methods for doing this are discussed below), optionally placing the bag/sleeve combination in a container (such as a prior art type of aerosol container), and then filling bag 110 through its valve under pressure, precisely as is done with prior art aerosol products.

In some embodiments, a bag 110 may be filled, at least in part, before bag 110 is subjected to pressure from sleeve 200. For example, FIG. 3 is a simplified schematic of an alternative filling scheme, using components known in the industry as "Bag in can", or "BIC", according to an embodiment of the invention. Filling stages 1-6 are shown in the figure.

Stage 1 shows an empty BIC pouch 112, a form of bag 110.

Stage 2 shows pouch 112 attached to a top plate 114, which will become the top of an aerosol can.

Stage 3 shows pouch 112 being filled with a material 115 to be dispensed. (Gravity or low-pressure filling is often used in BIC manufacture.)

Stage 4 shows a valve 120 added to top plate 114.

Stage 5 shows a sleeve 200 positioned around filled pouch 112. (Methods for accomplishing this are presented below.)

At stage 6, pouch 112 and sleeve 200 are together introduced into a can or canister 116, which is then attached to top plate 114, completing the assembly process.

Typical (non-limiting) dimensions for an exemplary embodiment:

Sleeve 200 length: 60-260 mm

Diameter of lumen 250 before expansion: 4-8 mm

Thickness of sleeve 200 before stretching: about 2-3 mm

Diameter of lumen 250 after stretching (i.e. after filling of bag 110): 30-70 mm (BOV and BIC)

Figure 4:
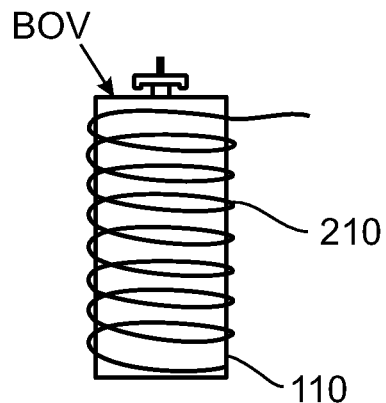
FIGS. 4 and 5 are simplified schematics showing alternative methods of construction of a sleeve, according to an embodiment of the present invention.
Figure 5:
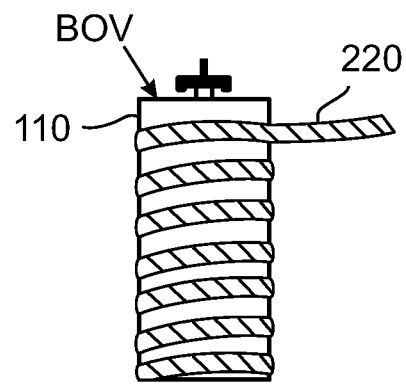

Alternative Constructions for Sleeve 200:

FIGS. 4 and 5 are simplified schematics showing alternative methods of construction of sleeve 200, according to an embodiment of the present invention. In FIG. 4, at least one spring 210, optionally of metallic or plastic construction, is used to compress a bag 110 (optionally, a BOV 150). Spring 210 may be a helical spring expanded beyond its natural resting position, and which therefore exerts a centripetal force on bag 110 so long as it is so expanded. This configuration is shown in FIG. 4. Alternatively spring 210 may be formed of geometrical shapes (for example, squiggles and polygons) arranged circumferentially and having a tendency to contract and thereby apply radial pressure to a volume within the spring(s), such as configurations used in medical stents.

In FIG. 5, a helical elastic band 220 is wrapped under tension around a bag 110, optionally from top to bottom. Elastic qualities of elastic band 220 cause it to apply centripetal pressure to bag 110 in a manner similar to that of solid sleeve 200 shown in FIG. 2.

It is to be noted that FIGS. 1-5 present several examples of types of sleeve 200. These examples are exemplary only, and should not be considered limiting. In some embodiments sleeve 200 may be an extruded rubber tube, or a rubber tube made in some manner other than extrusion, and/or may be made of other elastic materials (for example Silicone, Polyethylene, EPDM, EP, SBR, Natural Rubber, and similar materials) or a combination of materials, may comprise nanoparticles as discussed below, or may be constructed of one or more springs 210 or one or more elastic bands 220, or comprise a combination of these and/or other elements capable of containing a bag 110 and exerting and sustaining an elastic force towards bag 110 while at least partially surrounding it. In some optional embodiments, it is contemplated that a sleeve 200 may be presented in an airtight container (closed at ambient pressure or at a slightly higher pressure, for example a pressure between 1-1.5 bar) which will present some resistance to shocks or pressure from outside sources. Most of the exemplary embodiments presented by the figures herein comprise a sleeve 200 cut to a selected length from a long tube of continuously extruded rubber, but this embodiment is exemplary and not limiting, and the word "sleeve" and the designation "sleeve 200" should be understood to include all embodiments mentioned in the present paragraph, and all embodiments which are physically similar or have similar effects.

Exemplary Pressure Ranges:

With reference to the amount of pressure made available by sleeve 200, for some uses, called "low pressure" applications herein, such as for example, dispensers for food or food components, cosmetics, medicines, salves, creams, ointments, glue, toothpaste and the like, a maximum pressure of 1.5-4 bar when bag 110 is full may be appropriate. Optionally, for aerosol applications, pressure in the neighborhood of 7-8 bar when bag 110 is full is considered appropriate, with a minimum pressure optionally falling two between 2-5 bar as the device is emptied. For some applications, higher pressures are indicated: between 10 and 20 bar might be indicated for a fire extinguisher, for example. All such pressure ranges, and indeed any pressure above room pressure and up to 20 bar or more may be appropriate as embodiments of the present invention, though those specific ranges are not to be considered limiting. Embodiments delivering a material at low pressure but at a fast rate, or at high pressure but at a slow rate, are also contemplated.

Providing Residual Pressure as Bag Empties:

With reference to the minimum pressure provided by sleeve 200, in some embodiments little or no significant pressure is applied by sleeve 200 to bag 110 unless and until bag 110 is filled or partially filled with a dispensable material 115. However, in some embodiments, sleeve 200 provides a minimum pressure, for example a pressure of between 1.5 and 4.5 bar, even when bag 110 is empty, and that pressure rises when bag 110 is filled. One possible purpose of this minimum pressure, which is the residual pressure that remains when bag 110 empties out during use, is to force substantially all or almost all of contents 115 to exit bag 110 as bag 110 empties out. Under that residual pressure, free-to-flow contents of bag 110 will find their way to valve 120, if valve 120 is held open and every other flow direction encounters a residual pressure of somewhere between 1.5 and 4.5 bar. It should be noted that this fact constitutes a potentially significant advantage of low pressure embodiments over prior art low-pressure systems, where the difficulty of getting the last bit of contents out of, say, a ketchup bottle or a toothpaste tube, are well known to all.

For many embodiments it may be considered desirable to minimize the difference between maximum and minimum pressures, but in general these values will be chosen with specific uses and materials in mind. Some exemplary ranges include max/min pressure values of about 8/3 or 7/3 or 9/3.5, the choice for a particular application depending, among other considerations, on the viscosity of the material and the delivery rate that is required. A pressure of 8 bar, diminishing to 3 bar as bag 110 empties, may be considered to provide adequate performance for some aerosols.

Attachment of Sleeve to Bag or 'BOV':

In some embodiments a first end portion of a sleeve is positioned so that it surrounds a portion of the BOV valve assembly structure 130 (or any other structure that comprises a valve and attaches that valve to a bag), so that pressure applied by the sleeve end portion on the valve assembly structure binds sleeve, valve, and bag to each other. In some embodiments that pressure and induced friction between sleeve and valve assembly structure 130 suffice to hold the two together, though some movement may take place during construction or operation. This arrangement comprises a method for mounting sleeve and BOV (or other bag and valve module) together, and is convenient for manufacture because no gluing, welding, screwing, crimping, nor other similar methods of attachment are needed. (Optionally, a pressure adhesive can be used.)

Figure 6:
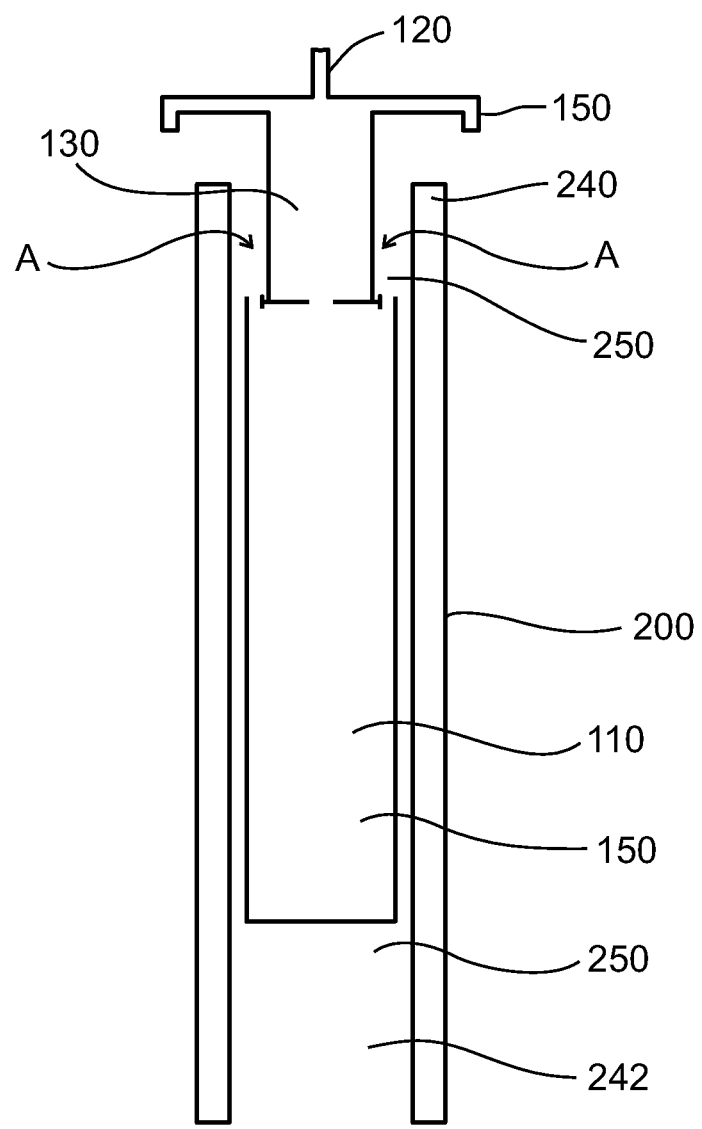
FIG. 6 is a simplified schematic showing details of a method for mounting a sleeve and bag so that they are anchored to each other, according to an embodiment of the present invention.

FIG. 6 is a simplified schematic showing details of such a method for mounting a sleeve 200 and bag 110 (optionally a BOV 150) so that they are anchored to each other, according to an embodiment of the present invention. FIG. 6 shows a valve assembly structure 130 of a BOV or of any other configuration combining a valve 120 with a bag 110. Valve assembly structure 130 contains valve 120, connects to bag 110, and possesses a surface which can come in contact with a top end region 240 of sleeve 200. In some embodiments, as discussed in detail herein below, during manufacture of dispenser 100 sleeve 200 is caused to expand so that bag 110 may be inserted therein. In some embodiments valve assembly structure 130 is also introduced into internal lumen 250 of sleeve 200. On the figure, for clarity, a space is shown at positions 'A' between valve assembly structure 130 and top end 240 of sleeve 200, as might be the case during insertion of bag 110 and structure 130 into sleeve 200. However, once insertion is completed and sleeve 200 is cause to relax, sleeve 200 optionally contracts around bag 110 and top end 240 of sleeve 200 optionally contracts around valve assembly structure 130, effectively grasping structure 130 and binding structure 130 and sleeve 200 together. (If desired, a spacer can optionally be added between bag and sleeve or between sleeve and valve assembly structure, to ensure a desired minimal pressure and/or contact quality.)

In some embodiments this optional method of construction can be significant, because of its simplicity: in some embodiments sleeve 200 is caused to expand, bag 110 and structure 130 are inserted, and sleeve 200 contracts, and no crimping, gluing, welding, snapping, screwing, or other complex forms of attachment are necessarily required.

Providing a Sleeve Longer than a Bag Contained in the Sleeve:

In some embodiments the sleeve is longer than the bag, so that when a top end of a sleeve is attached to a valve or to a portion of a bag near a valve, the bottom end of the sleeve) extends beyond the end of the bag.

FIG. 6 shows such a configuration. As seen in the figure, "top" end 240 of sleeve 200 (the end which will be near the valve) is positioned near and somewhat above the top end of bag 110, while the 'bottom' end 242 of sleeve 200 (also called "distal end 242") extends well below the bottom of bag 110. For example, in an exemplary embodiment using a bag 110 15 cm long from top to bottom, a sleeve 200 might extend between 1 and 2 cm below the bottom of bag 110.

This configuration may help to provide adequate pressure containment for the pressurized contents of bag 110, despite the fact that sleeve 200 is open at both ends. If sleeve 200 were no longer than bag 110 and open at top and/or bottom, the related top and/or bottom of bag 110 would be unsupported and subjected to a high pressure differential, with highly pressurized contents 115 within bag 110 and no support outside the bag ends. However, as may be seen in the optional configuration shown in the FIG. 6, sleeve 200 extends both above the top of bag 110 and below the bottom of bag 110. Since sleeve 200 is not expanded by pressure from bag 110 at this top and bottom ends, these ends tend to be forced into a somewhat funnel-like configuration, as may be seen in FIG. 2. Material from bag 110 (and in particular the content-empty supporting edges of the bag of a BOV according to standard BOV manufacture) may 'bunch up', folding upon itself within these funnel-like end sections above and below the content-filled portions of bag 110, where they may provide support and strength in these end regions which would otherwise receive less direct support than that received by the sides of bag 110, since sleeve 200 presses directly on the sides of bag 110 but does not press directly on the ends of bag 110 because of the open-ended construction of sleeve 200. In some embodiments wherein a standard BOV bag is used, it is the non-fillable bag material which surrounds the fillable portion of the bag which may bunch up near valve assembly structure 130 and within distal end 242, where it adds sufficient support to enable bag 110 to hold contents pressurized to 7 or 8 bar or higher without danger of a 'blowout'.

(Optional additional methods for providing support for portions of bag 110 at positions near an open end of sleeve 200 include positioning a foam spacer or similar object within the sleeve end, closing or partially closing an and of sleeve 200 by cutting or folding its end, adding an end-cap, and providing a funnel-shaped end portion of bag 110 so that it better conforms to sleeve 200.)

Figure 7A:
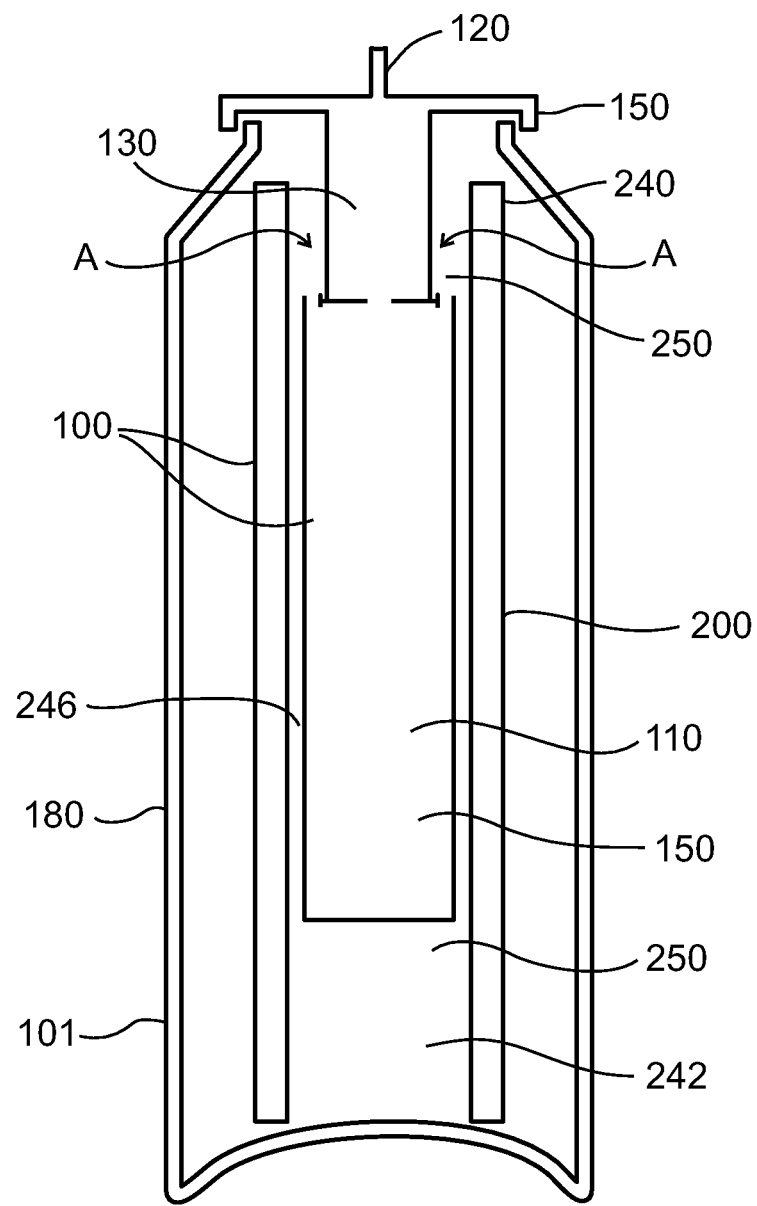
FIG. 7A is a simplified schematic of a delivery module combined with a container, according to an embodiment of the present invention.

An additional potential advantage of a configuration in which distal end 242 of extends beyond a distal end of bag 110 is shown in FIG. 7A, which is a simplified schematic of a delivery module 100 combined with a container 180 to form a contained dispenser 101 (also called a contained delivery module 101 herein), according to an embodiment of the present invention.

In some embodiments bag 110 and sleeve 200 are contained in and attached to an external container, and the bottom end of sleeve 200 is sized so as to touch (and optionally be supported by) the bottom of that external container, which may optionally be shaped to facilitate this contact. This configuration may immobilize or inhibit movement of the sleeve within the container, and may provide support against gravity for the sleeve/bag combination, which in some embodiments may be filled with 200-500 grams or more of material 115. Without support provided to delivery module 100, bag 110 would be left hanging on the valve assembly, and would be in danger of tearing off that assembly, resulting in catastrophic decompression, if the package were mishandled or subject to sudden acceleration, for example if it were to fall and sharply strike a hard floor.

FIG. 7A shows a configuration which may solve this potential problem. To the configuration of FIG. 6, a container 180 has been added. Note the position of distal end 242 with respect to container 180: in some embodiments, the length of sleeve 200 is adjusted so that distal end 242 can rest on the distal (i.e. the bottom) end of container 180. In this position end 242 provides support for bag 110, whether bag 110 is empty or full. (Note: in FIG. 7A a slight separation is present for clarity of the figure, but it is to be understood that in some embodiments, distal end 242 touches the bottom of container 180 and is supported by it.) This configuration may be contrasted to some configurations of prior art, in which an expandable bag containing content to be dispersed hangs unsupported from its connection near a valve, and swings around within its container without support from beneath it.

Figure 7B:
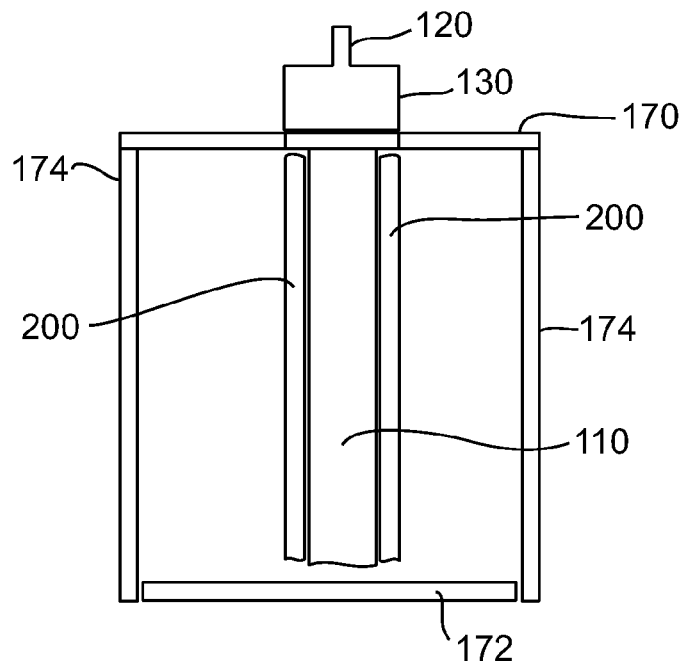
FIGS. 7B and 7C are simplified schematics of an alternative arrangement for bag and sleeve, according to an embodiment of the present invention.
Figure 7C:
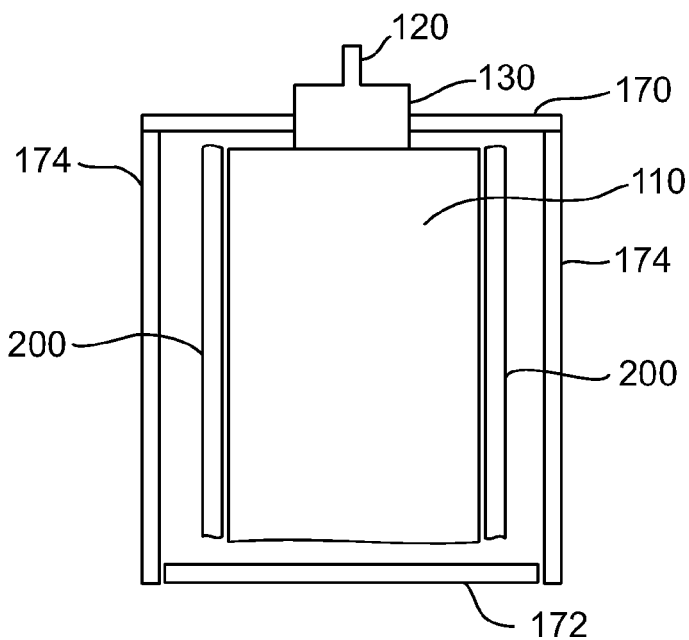

Alternative Embodiments with Sleeve and Bag of Similar Lengths:

FIGS. 7B-7C are simplified schematics of an alternative arrangement for bag and sleeve, according to an embodiment of the present invention. In an embodiment shown in these figures a sleeve 200 has approximately the same length as a bag 110.

FIG. 7B shows bag 110 empty, and a loose or partially contracted sleeve 200 around it. Above bag and sleeve, a top disk 170 is provided, optionally attached to a valve assembly structure 130, or optionally attached to sleeve 200. Below bag and sleeve, a bottom disk 172 is provided, also optionally attached to sleeve 200. Optionally, top disk 170 may be attached to a rod or cable connecting top disk 170 to bottom disk 172. In another option, disks 170 and 172 may optionally be components of or attached to an external container 180.

FIG. 7C shows the same embodiment after bag 110 has been filled, causing sleeve 200 to expand laterally. Top disk 170 and bottom disk 172 are designed to provide adequate support to top and bottom of bag 110 under conditions of the pressure exerted by sleeve 200 on bag 110. While the contents of bag 110 are under pressure from sleeve 200, lateral walls of bag 110 are not in danger of a 'blowout' because pressure exerted outward by contents of bag 110 meet an equal pressure exerted inward by sleeve 200. However since sleeve 200 is optionally open at one or both ends, the top and/or bottom of bag 110 could be subject to outward pressure from contents of bag 110, not matched by inward pressure of sleeve 200. Top disk 170 and bottom disk 172 are provided to support the top and bottom of bag 110.

Top disk 170 and bottom disk 172 are optionally embodied as top and bottom of an external container 180. Optionally, sides 174 may also be provided outside sleeve 200 to hold disks 170 and 172 in place, and these may optionally be sides of an external container 180.

Compatibility with Existing Systems:

In some embodiments, a delivery module 100 (including bag 110, valve 120 and associated hardware, and sleeve 200) is sized to be insertable into a container sized and shaped as an aerosol can, for example an aerosol can such as is used in prior art devices which use a gas propellant. In some embodiments, during device manufacture, a bag (e.g. a BOV) is inserted into a sleeve during expansion of the sleeve as described above, then the bag and sleeve combination is inserted in a can, then the bag is filled through the valve under pressure from the material source. The bag-filling process is therefore optionally similar to the way BOV bags have traditionally been filled, and standard filling machines can be used with some embodiments of the present invention with relatively minor modifications. Indeed, the filling process is potentially simplified because with some embodiments of the present invention the stages of filling with propellant and testing for leaks are eliminated, and since the joining of bag and sleeve to external container is not pressure-sensitive, crimping is unnecessary and can optionally be replaced by a simpler and cheaper methods of attachment.

In some embodiments a BOV bag, wrapped around itself and contained in a sleeve 200, can optionally be made small enough to pass through the standard opening (about 1" diameter) made to fit the standard top of a BOV, making these embodiments compatible with a size standard of the aerosol industry. As shown in the FIG. 7, a container 180 is positioned for connection to such a top. Using a bag and sleeve which can be inserted into an external container and then subsequently filling the bag not only enables a manufacturer to use existing production lines with relatively minor changes, it also optionally enables a manufacturer to use existing containers (e.g. existing aerosol cans, for existing product lines, having standard-sized openings on top, graphics designs familiar to customers, etc.) and existing BOVs, valves, and other parts, while yet producing and selling embodiments of the present invention. Similarly, BIC containers can be used and BIC production sequences can be used with minor modifications.

Ease of Attachment of Pressure Despenser to an External Container:

Prior art aerosol cans contain a propellant under pressure. Consequently, when attaching a BOV or other bag arrangement to an external container, care must be taken to provide a solid and reliable airtight connection able to withstand aerosol pressures, which are typically in the 7-8 bar range. Accordingly, aerosol valve assembly structures typically comprise a solid cap with a gasket, which is attached to the body of an aerosol can by crimping, or by a similar process, to produce a reliable seal able to stand up to high pressure without leaking. The materials and process involved add cost and complexity as compared to some means and methods which may be used to attach a pressure dispenser 100 to a container 180. Since according to some embodiments of the invention pressure is supplied a tendency of elastic sleeve 200 to contract to its resting state, no gas pressure need be maintained within container 180. Therefore in some embodiments, a BOV 150 or other pressure dispenser 100 can be attached to an external container 180 using lighter, simpler, and cheaper materials and/or methods than those used by the prior art. For example, a standard P.E.T plastic can be used, with one part simply snapping to another, or one part screwing into another, or a glue or any other simple attaching mechanism can be used. This fact makes this attaching process cheaper and simpler than those required to connect a BOV to a container according to methods of prior art.

Optionally, container 180 may be made airtight, e.g. containing air at room pressure or at somewhat elevated pressure, so as to help it withstand external impacts to which a product might be subjected during distribution or during use.

Optionally, container 180 may be made intentionally not airtight, for example to prevent pressure differentials in low or high pressure contexts such as air transportation or decompression chambers.

Freedom in Design of External Container:

Since in some embodiments container 180 is not required to hold a pressurized propellant, these embodiments are neither practically nor legally required to be of cylindrical shape and/or to be very solidly constructed, as is the case for at least some prior art aerosol containers. As a result, some embodiments may comprise external containers 180 which are constructed of weaker, cheaper, and simpler materials (for example P.E.T, carton, glass, thin metal), and/or using simpler and more economical construction processes, than those which can be used by aerosol containers according to prior art. In consequents, products which comprise embodiments of the present invention may be constructed in a variety of external shapes selected according to aesthetic or marketing or other considerations. Embodiments comprising containers of a variety of shapes and materials are contemplated. For example, curved shapes, shapes which are triangular, hexagonal, rectangular, oval, other geometric shapes, shapes which are concave on multiple sides, have straight sides, or have sides which are combine concave and/or convex and/or straight sides, and entirely irregular shapes may be selected and used for aesthetic reasons, to individualize or draw attention to a product, to facilitate packing and handling, or for a variety of commercial reasons. In contrast to the practical and in some cases regulatory limitations of prior art aerosol containers, some embodiments of the present invention are optionally present an aerosol or other pressure dispenser 100 in one of the shapes mentioned in this paragraph or in other non-cylindrical shapes.

Sleeves with Multiple Layers of Strips of Sections:

Attention is now drawn to FIGS. 8A-8D, which are simplified schematics of sleeves 200 which comprise multiple layers and/or multiple strips of elastic material, according to embodiments of the present invention. Such sleeves are labeled 209 in FIGS. 8A-8D, but it is to be understood that any of sleeves 200 mentioned herein can be constructed utilizing multiple layers and/or multiple strips of differing material compositions. Such multiple layers or strips can optionally be extruded together, or a layer can be applied or attached or sprayed or painted onto an existing other layer to make a sleeve 209, or a sleeve or sleeve portion can be used as a mold for injection molding. Optionally, sleeves can be stretched during any of these processes. Optionally, layers and surfaces need not necessarily be flat but can be created with undulations or other surface features.

Note that these figures are not to scale, some layers being of exaggerated thickness in the figures, for clarity of the drawing. Also, it is to be understood that any of the various features presented separately in FIGS. 8A-8D may also be used in combination, and may be used in conjunction with any of the various embodiments described herein.

Embodiments without Containers

Figure 8A:
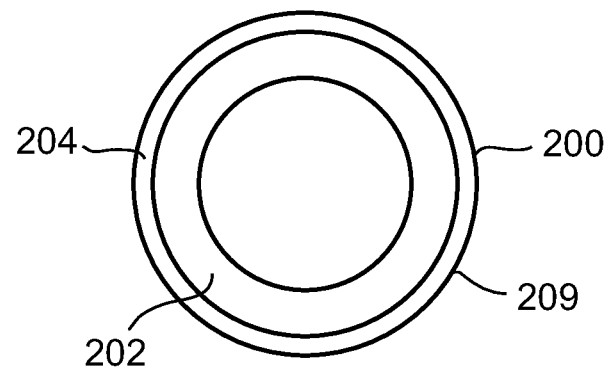
FIGS. 8A-8D are simplified schematics of sleeves which comprise multiple layers and/or multiple strips of elastic material, according to embodiments of the present invention.

In some embodiments, a sleeve 209, optionally produced by a multi-layer extrusion process or by an attaching or painting or spraying or molding or similar process, provides an external layer having selected aesthetic characteristics (e.g. desirable shape, color, surface texture, etc.) or mechanical characteristics (e.g. a non-slip surface, adaptation to particular environmental conditions) covering a sleeve body whose physical characteristics are optionally chosen to enhance its elastic and energy-storing capacity. FIG. 8A presents a cross-section of a sleeve 200 with an inside layer 202 designed to enhance its elastic energy-storing capability, surrounded by an outside layer 204 designed for selected aesthetic and/or tactile qualities and/or other presentational qualities, which can be produced simultaneously by a combined extrusion process.

Embodiments without Independent Bags

Figure 8B:
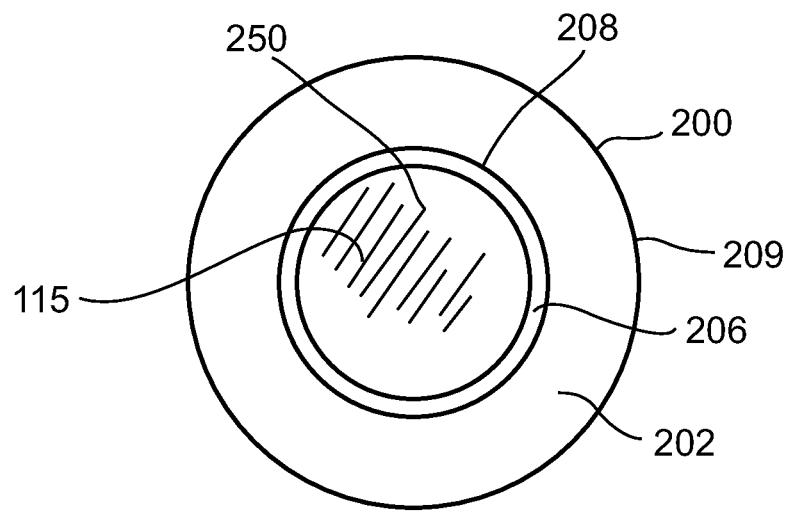

In some embodiments, a sleeve 200 comprises layer 206 (which may be thought of as a surface or a coating) covering an inner wall 208 which defines a lumen 250 within a sleeve 200. Layer 206 can be designed, for example, to minimize or prevent interaction between a material 115 introduced into lumen 250 and elastic material comprising a layer 202 made of material selected for its elastic energy-storing capabilities. In these embodiments, layer 202 may be porous and/or may react with a material 115, and layer 206 may be designed for impermeability and for minimal reactivity. FIG. 8B can be used to produce an embodiment in which a material can be stored under pressure and dispensed through a valve, wherein layer 206, though an extruded layer of sleeve 200, serves as bag 110 and provides the functionality of bag 110 as described herein. (In some of these embodiments, where layer 206 functions as a bag 110, lumen 250, within layer 206, will be closed at least at its bottom, e.g. by welding or gluing of the bottom and optionally the top ends of sleeve 200, optionally to top and bottom disks similar to those shown in FIGS. 7B and 7C or to a cap of similar construction.)

Figure 8C:
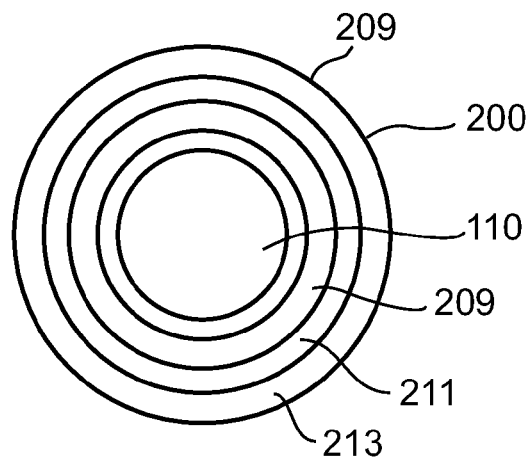

Embodiments which Combine Extruded Strips or Layers to Tailor Expansion Characteristics In some embodiments multi-layer extrusion is used to create a sleeve in which each of a plurality of layers, strips, or regions combines different properties of elasticity, strength, and/or different resting diameters, and/or differences in other physical characteristics which cause them to respond differently under applied force and/or thermal energy and/or electric potential, or which differ in other physical properties. FIG. 8C is constructed with a multi-layer extrusion wherein each of a plurality of layers (in the figure, layers 209, 211, 213) has different physical properties. In some embodiments 2, 3, 4, or more layers may be used, and in some embodiments a continuous variance of physical characteristics over all or part of an extrusion cross-section or extrusion length may be used.

Figure 8D:
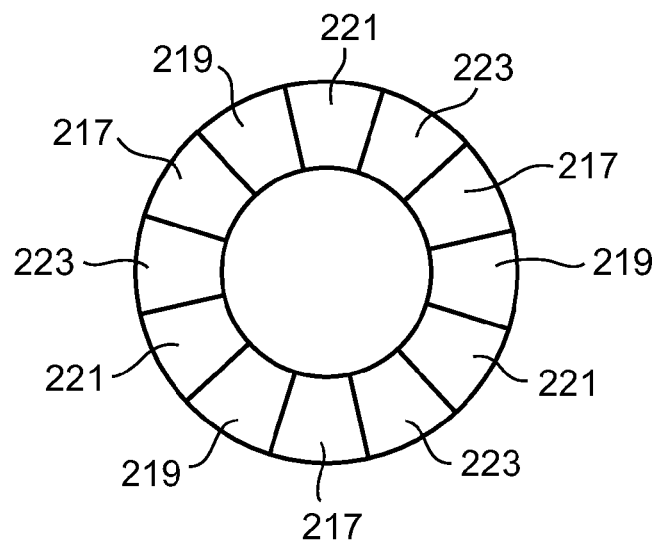

In some embodiments multi-material extrusion is used to create a sleeve in which each of a plurality of regions (optionally longitudinal strips) have different properties of elasticity and strength and/or different resting diameters, and/or differences in other physical characteristics which cause them to respond differently under applied force. Such strips can optionally be combined to produce an elastic performance with desirable characteristics. Such a structure is shown in FIG. 8D, and may be used, for example, to produce a sleeve 200 which provides a relatively uniform amount of pressure under differing conditions of expansion, thereby creating a dispenser with relatively uniform performance (pressure, dispensing rate), while, during use, a bag 110 contained within is gradually emptied of its contents. FIG. 8D is optionally constructed with a multi-strip extrusion wherein each of a plurality of strips (in the figure, strips 217, 219, 221, 223) has different elastic properties.

Embodiments with Sleeves with Selected External Shapes

Figure 8E:
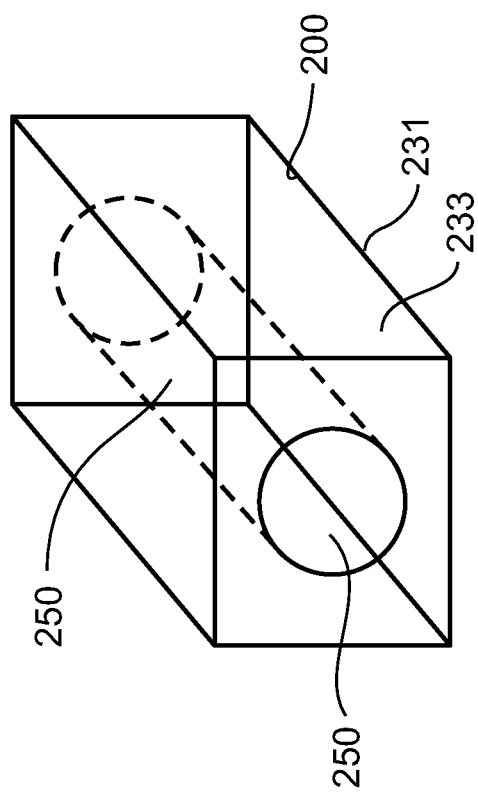
FIG. 8E is a simplified schematic of a sleeve having an external shape which differs from a shape of its internal lumen, according to an embodiment of the present invention.

Attention is now drawn to FIG. 8E, which is a simplified schematic of a sleeve 200, here labeled sleeve 231 having an external shape which differs from a shape of its internal lumen, according to an embodiment of the present invention. In the exemplary embodiment shown in the figure, lumen 250 is of circular cross-section, whereas external wall 233 of sleeve 221 is of square cross section. It is to be understood that these shapes are exemplary and not limiting. External shape of sleeve 221 might, for example, be triangular, or oval, have convex and/or concave sides, or have some other geometric or irregular shape. Embodiments with sleeves 200 with designed external shapes optionally different from shapes of internal lumen 250 of the sleeves may be used with external containers (which they are optionally designed to fit) or without external containers (optionally with an external surface 'presentational' layer, as described in FIG. 8B.

Use of Enhanced Rubber:

When pressurizing a bag of deliverable material by means of an elastic sleeve 200, it can be useful to have a sleeve with a high elasticity modulus, providing a high energy storage density. In some embodiments, threads or narrow bands or other connecting or elastic materials may be added to a rubber or other material to enhance elastic characteristics of a sleeve.

In some embodiments, nano-particles of clay or other materials are added to rubber used to construct sleeve 200. In general, rubbers having high ultimate elongation have low modulus. In some embodiments, a reinforcing material is incorporated in a rubber, to increase rigidity of the rubber while enabling a desired level of elongation (elasticity). In some embodiments nano-particles are used as the reinforcing material.

Selection of quantity and type of nano particles and/or other reinforcing materials, and methods of processing them, may depend on desired performance characteristics and/or thickness or other desired physical characteristics of an apparatus designed for a particular application.

The published articles listed below describe research in this field. The Stress-Strain curves shown in each article compare various rubber formulations with and without nano particles. They show lower stress-strain curves showing performance of a rubber without nano-particles, as a control groups, and upper curves showing stress-strain performance of formulations combining rubber-based composition with nano particles such as Nanoclay (NC), Graphene, Nanosilica (NS) and Carbon Nanotubes (CNT). As the experimental results show, these formulations provide improved modulus at adequate elongation. As may be seen from the curves shown in the articles, nano-particles dramatically increase the elasticity modulus of a rubber, for which reason in some embodiments we use them in rubber used to construct sleeve 200. In some experiments tensile strength of 20 MPa was achieved with rubber of 1.5-2.0 mm thickness, which is well beyond what normal rubber without nano particles can achieve. (Stress-strain curves in the following articles are based on standard material test procedures using material of 1.5 mm to 2 mm thickness.) Embodiments in which sleeve 200 is constructed of rubber treated with nano particles can compress a bag 110 to 7-8 bar of pressure, using a sleeve as little as 3 mm thick. In other words, addition of nano particles to rubber enhances the capacity of that rubber to serve as an energy storage device.

Here are the articles:
- Amit Das, Francis Reny Costa, Udo Wagenknecht, Gert Heinrich. *Nanocomposites based on chloroprene rubber: Effect of chemical nature and organic modification of nanoclay on the vulcanizate properties*, European Polymer Journal 44 (2008) 3456-3465, available at www.elsevier.com/locate/europolj;
- Das, R. N. Mahaling, K. W. Stöckelhuber, G. Heinrich. *Reinforcement and migration of nanoclay in polychloroprene/ethylene-propylene-diene-monomer rubber blends*. Composites Science and Technology, Issue 71 (2011), Pages 276-281, available at www.elsevier.com/locate/compscitech;
- Yoong Ahm Kim, Takuaya Hayashi, Morinobu Endo, Yasuo Gotoh, Noriaki Wada, Junji Seiyama. *Fabrication of aligned carbon nanotube-filled rubber composite*. Scripta Materialia, Issue 54 (2006), Pages 31-35, available at www.sciencedirect.com; and
- Xin Bai, Chaoying Wan, Yong Zhang, Yinghao Zhai. *Reinforcement of hydrogenated carboxylated nitrile-butadiene rubber with exfoliated graphene oxide. Carbon*, Volume 49, Issue 5, April 2011, Pages 1608-1613, available at www.elsevier.com/locate/carbon.

Some Specific Uses:

In some embodiments a bag/sleeve combination is formed as a transfusion module operable to provide gravity-independent transfusions of blood and/or other liquids into to the blood stream of a patient, e.g. in hospital and in first-aid situations. Such an embodiment can provide greater comfort to a patient, eliminating the need for IV stands and long trailing tubes beside the bedside, but rather can optionally be positioned near the transfusion site and taped or otherwise conveniently attached to the limb of a patient, who is then able to move around with less difficulty than using prior art transfusion methods. Emergency transportation of patients could also be greatly facilitated using such a module.

Transfusion modules can adapted to providing transfusion materials at selected pressures, e.g. to simulate a standard hospital drip bag, or alternatively to provide a rapid transfusion source for emergency situations.

Figure 8F:
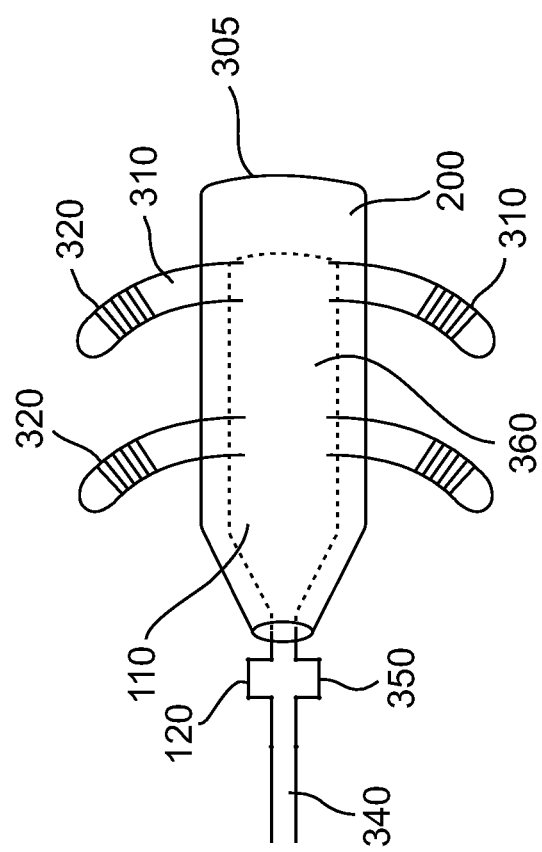
FIG. 8F is a simplified schematic of a transfusion module 305, according to an embodiment of the present invention.

FIG. 8F is a simplified schematic of a transfusion module 305, according to an embodiment of the present invention. Module 305 comprises a bag 110 filled with blood or other transfusion fluids, a sleeve 200 compressing bag 110 at a desired pressure, and optionally comprises or connects to a valve 120 (which may be embodied as a mechanical valve and/or an electronic dosage machine and/or another dosage control mechanism) formed as a dispensing control 350 for controlling delivery rate of the transfusion fluid, and optionally comprises attachments 310, (optionally, straps comprising Velcro attachments 320 or something similar) for attaching module 305 to a bed or stretcher or to a patient's body. In some embodiments a pressure of between 1.5 and 4 bar is used in module 305. In the opinion of some physicians, residual pressure in module 305 should not fall below 1.5 bar as bag 110 of module 305 empties out. Maximum pressures selected for module 305 may depend on its intended use, and depend on the viscosity of the material being transfused and the desired delivery rate. For example, a sleeve providing between 4 and 6 bar of pressure might be used, or a sleeve providing 2-3 bar of pressure might be used with a dispensing control 350 which is able to provide a high deliver rate.

Exemplary Construction Methods:

Some embodiments comprise methods and apparatus for manufacturing devices as described hereinabove. In some embodiments sleeves 200 are provided with graspable fins or other forms running along the length of the sleeve, or other graspable shapes (for example, the corners of a square or triangular shape) comprised on a sleeve, integral to the sleeve or attached to it, and during construction these graspable shapes are grasped and pulled away from each other by a mechanism which thereby expands the sleeve so that a bag (e.g., full or empty) can be inserted therein. In some embodiments a set of rods or other thin, elongate and optionally bend-resistant elements are inserted into the lumen of a sleeve, and then are pulled apart, expanding the sleeve and enabling insertion of a bag. In some embodiments high pressure within a sleeve and/or low pressure outside a sleeve expand the sleeve and enable bag insertion.

Figure 9:
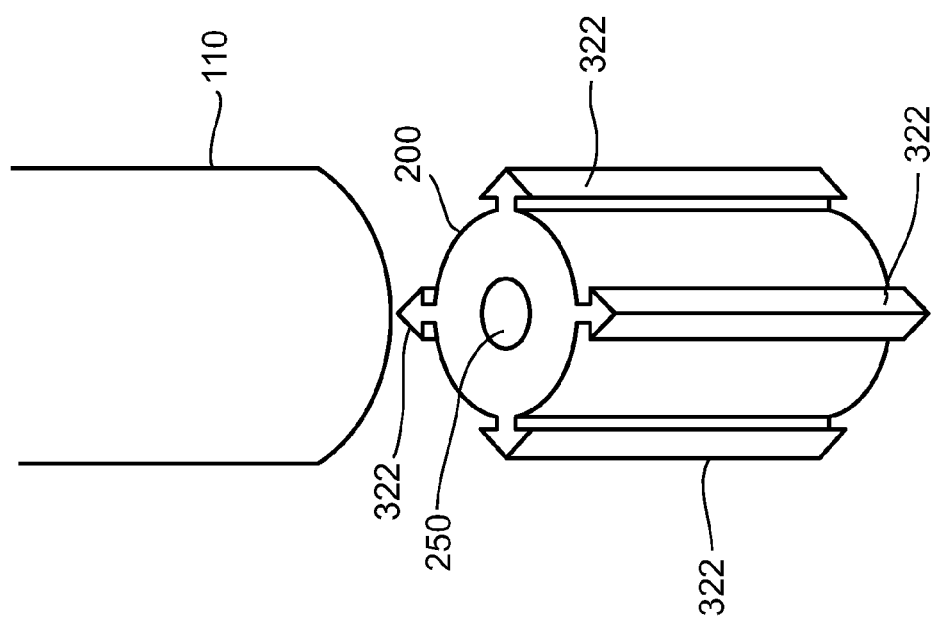
FIGS. 9-11 are simplified schematics showing a method for expanding a sleeve by pulling its sides outward during a manufacturing process, according to an embodiment of the present invention.
Figure 10:
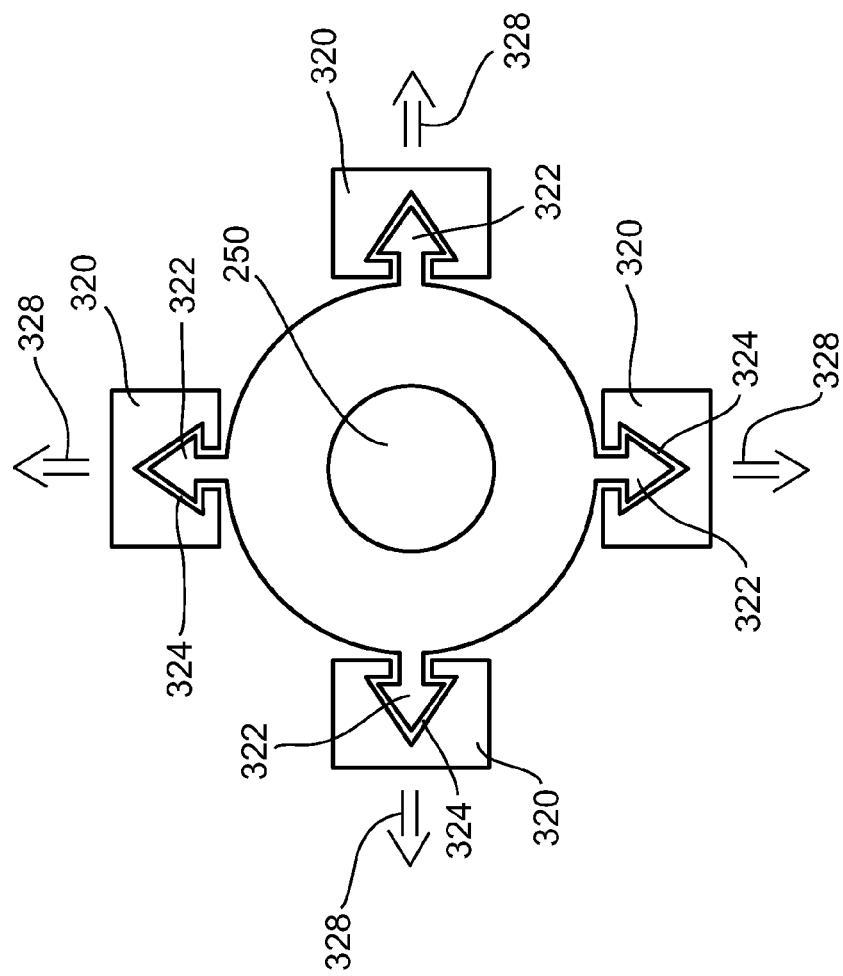
Figure 11:
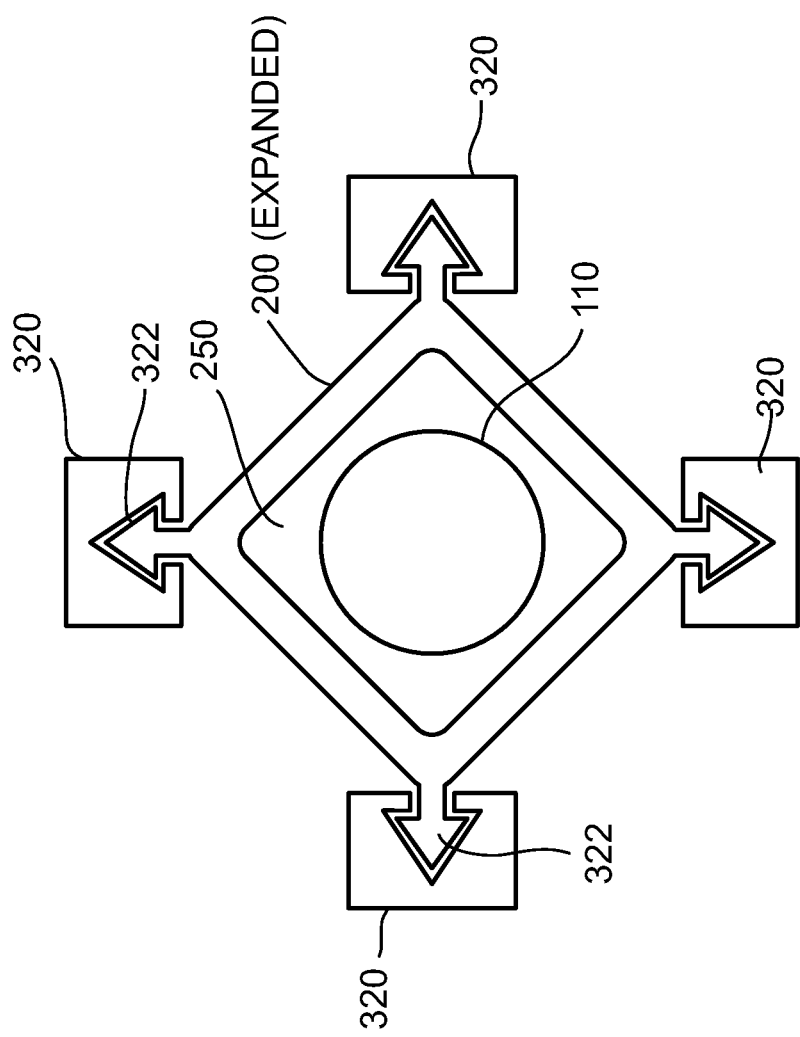

Attention is now drawn to FIGS. 9-11, which are simplified schematics showing a method for expanding a sleeve 200 by pulling its sides outward during a manufacturing process, according to an embodiment of the present invention.

FIG. 9 presents the problem to be solved: in some embodiments it is desirable that sleeve 200 provide residual pressure on bag 110 even when bag 110 is empty or nearly empty. To accomplish this, in some embodiments it is necessary to introduce bag 110 into internal lumen 250 of sleeve 200, although that lumen has a diameter smaller than the diameter of rolled-up bag 110. This situation is shown in FIG. 9.

An exemplary solution is presented in FIG. 10. In some embodiments an assembly apparatus (not shown in its entirety) comprises a set of at least three grippers 320. Grippers 320 are designed to grasp graspable shapes 322, which are part of or attached to sleeve 200, as shown in FIG. 9. In some embodiments graspable shapes 322 are constructed as continuous extensions from an external wall of sleeve 200. In some embodiments sleeve 200 is constructed by an extrusion process which produces a long tube which is subsequently cut into segments of a length appropriate for a specific application. Graspable shapes 322 are optionally constructed as integral parts of sleeve 200 extending outward and formed in a shape which is convenient for being grasped and pulled by grippers 320. In some embodiments, shapes 322 are simply corners or other graspable portions of sleeve 200.

In some embodiments grippers 320 may have jaws or surfaces which come together to grasp all or parts of shapes 322, and to pull them, optionally moved by a motor or servo-mechanism such as a robotic arm.

In some alternate embodiments, for example in an embodiment shown in FIG. 10, shapes 322 of sleeve 200 comprise a thick portion (e.g. the arrowhead shapes of shapes 322 in FIG. 9) connected to a narrower portion (e.g. the short arrow bodies connected to the arrowhead shapes 322 in FIG. 9), and grippers 320 comprise a slot 324 sized and shaped for receiving therein, in a longitudinal sliding motion, at least the thick portions of shapes 322. (Optionally, grippers can be moved to slide over the shapes, or the sleeve can be moved to slide the shapes within the grippers.) These thick portions are able to slide longitudinally within slots 324 (i.e. in a direction perpendicular to the plane of FIG. 10, but are designed not to be pulled laterally from slots 324 under the pressures required to stretch sleeve 200 sufficiently to insert bag 110 (empty or full, depending on the application and dispenser design), and the narrow portions are designed to resist tearing under pressures required to expand sleeve 200 to that extent. Consequently, pulling a gripper 320 laterally away from an extension 322 engaged within it (i.e. in the direction of arrows 328), results in pulling a portion of an external wall of sleeve 200 away from the center of sleeve 200. To insert a BOV into a sleeve 200, expansion of the sleeve to a diameter of a bit more than an inch may suffice, since the sleeve/BOV combination may in some embodiments be expected to be introducible into a aerosol can with a standard one-inch opening. The degree of expansion sufficient to enable placing the pouch of a BIC within a sleeve will typically be much larger, and may approximate the diameter of the can to be used.

During assembly of some embodiments grippers 320 equipped with jaws or the equivalent grip at least parts of shapes 322 and pull them as indicated by arrows 328. During assembly of some embodiments grippers 320 having slots 324 sized for graspable shapes 322 are slid over those shapes, and then pulled as indicated by arrows 328.

FIG. 11 shows the result: sleeve 200 is expanded, and lumen 250 becomes big enough to accommodate a bag 110, which can be inserted therein, (optionally using an introducer tube which is then retracted) after which sleeve 200 is allowed to relax, whereon it will apply pressure to bag 110. If a top portion of a BOV 150 comprising a valve assembly structure 130 is inserted within a top of sleeve 200, sleeve 200 will grasp and hold valve assembly structure 130, connecting sleeve to BOV, as explained earlier with reference to FIG. 6.

In prior art assembly methods, BOV bags are typically filled after insertion in a canister and pressurization of that canister. The optional method shown in FIGS. 9-11 produces a BOV/sleeve combination which can be inserted in such a canister, and then optionally filled, optionally under pressure through the valve, as is usual using the equipment and techniques usual in the aerosol industry today (the equipment optionally modified to in that no gas propellant is introduced). Alternatively, the method shown in FIGS. 9-11 can be used to stretch sleeve 200 sufficiently for inserting therein a filled bag 110.

Attention is now drawn to FIGS. 12-15, which are simplified images of an apparatus 400 for expanding a sleeve 200 by applying pressure from within lumen 250 outwards, according to an embodiment of the present invention. FIGS. 12-15 show a method which can be used to enable insertion of a bag 110 (filled or not yet filled) into sleeve 200.

Figure 12:
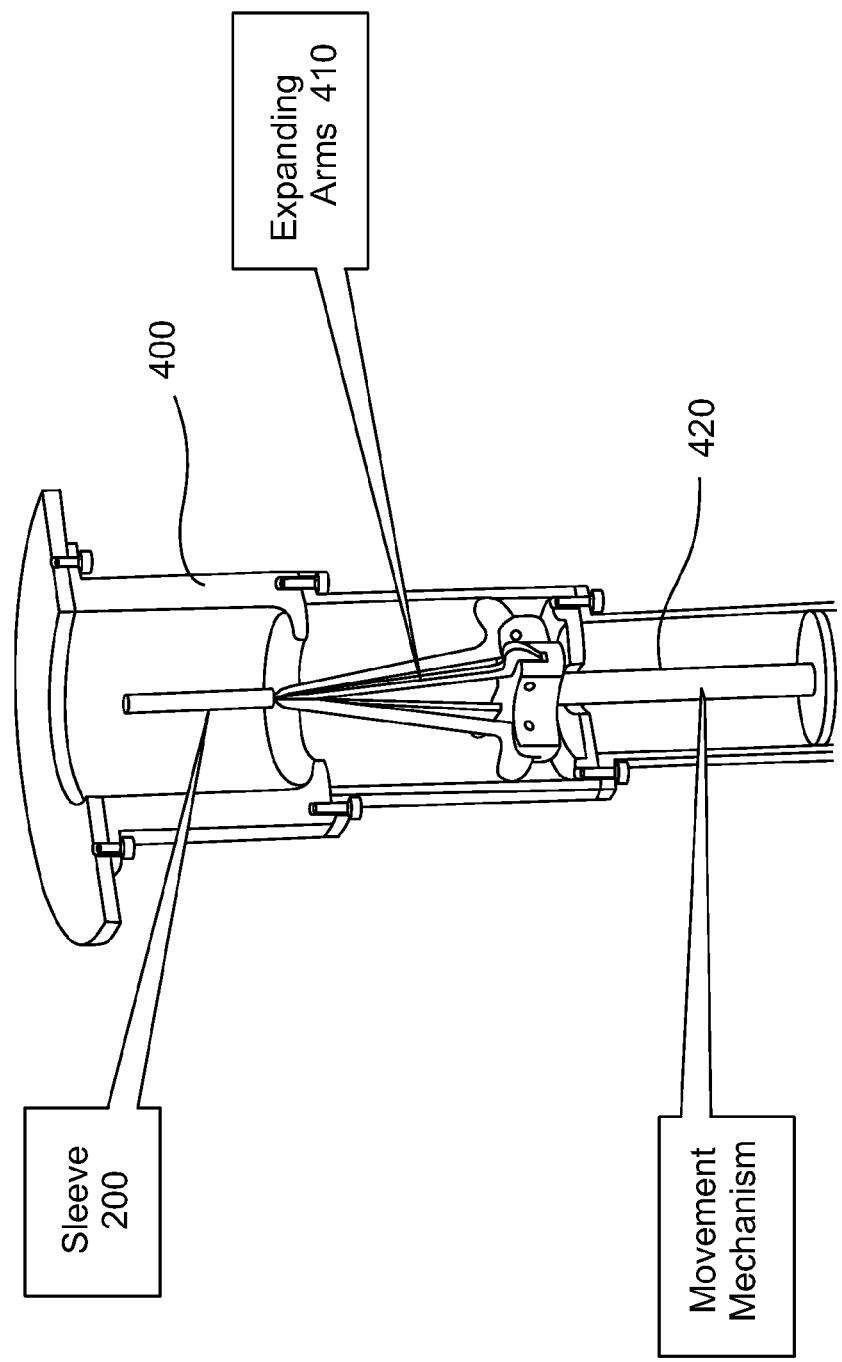
FIGS. 12-15 are simplified images of an apparatus 400 for expanding a sleeve by applying pressure from within outwards, according to an embodiment of the present invention.
Figure 13:
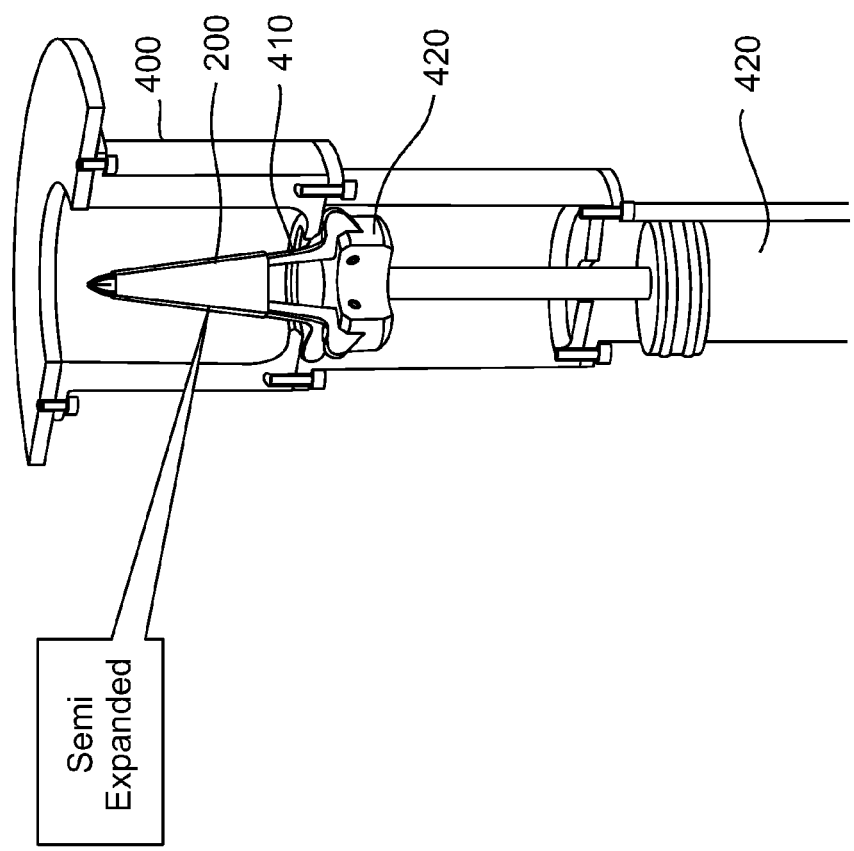
Figure 14:
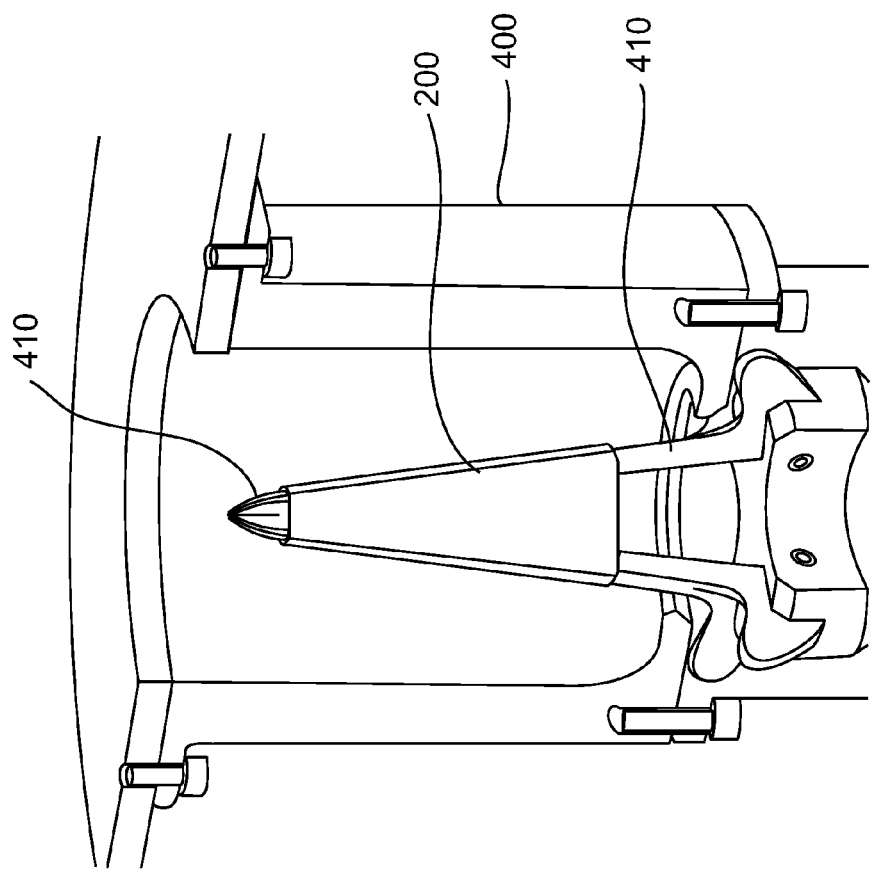
Figure 15:
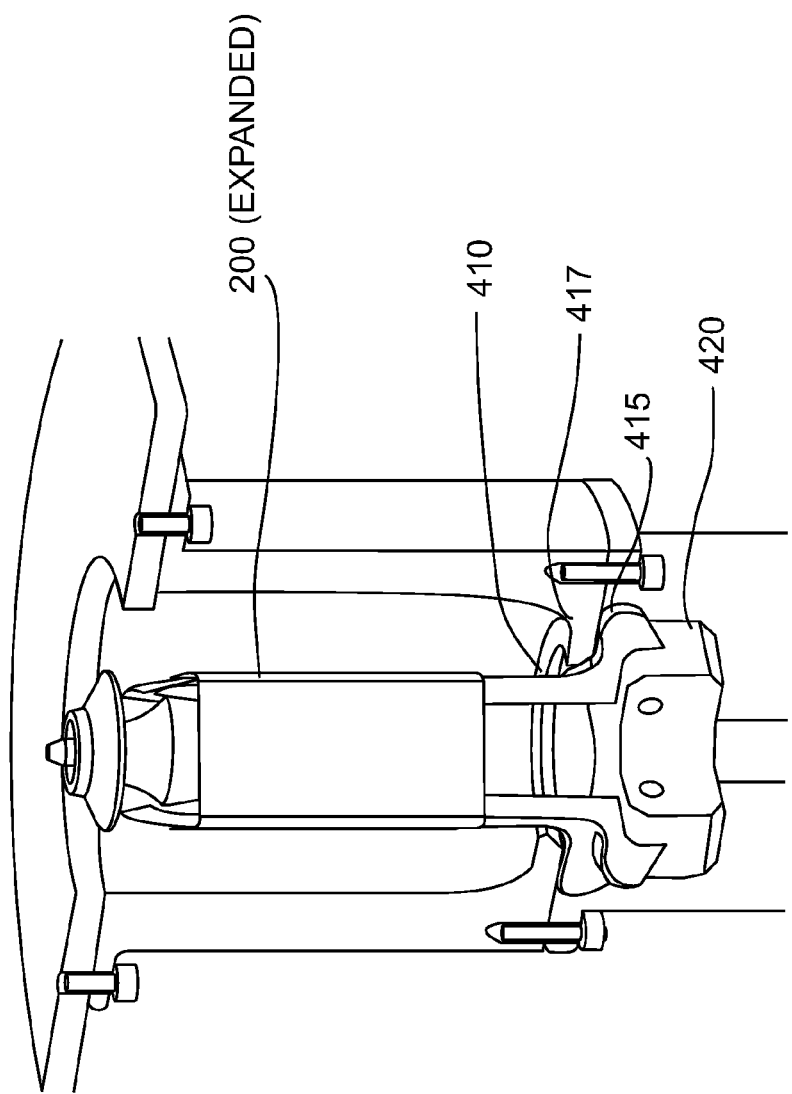

FIG. 12 shows a sleeve 200 positioned above a set of expanding arms 410 which can be pushed upwards by a movement mechanism 420. FIGS. 13 and 14 show two views of a stretching operation in progress, with sleeve 200 in a semi-expanded state. FIG. 15 shows sleeve 200 in an expanded state, arms 410 having been forcibly pushed outward from within lumen 250 as extensions 415 of arms 410 are pushed downward (as arms 410 are pushed upward) by extensions 417 of mechanism 400. It is to be understood that details of the embodiment shown in FIGS. 12-15 are exemplary only and are not to be considered limiting. Any mechanical arrangement for expanding sleeve 200 outward by exerting pushing pressure from within is considered an embodiment of the present invention, including pushing sleeve outward by means of arms or rods pushed from one end (as shown in the figure) or held and pushed from both ends, and also comprising pushing sleeve 200 outward by means of a pressure differential existing between lumen 250 and the environment outside sleeve 200.

Pushing the walls of sleeve 200 outwards and enlarging lumen 250 enable to insert a bag 110 into lumen 250. Relaxing sleeve 200 after insertion of bag 110 exerts pressure on bag 110 and, optionally on a valve assembly structure 130 associated with bag 110, as described above.

In some embodiments bag 110 is inserted in sleeve 200, then optionally positioned in a container, then filled under pressure. This process is optionally compatible with standard BOV filling procedures, with the exception of the process described above for inserting bag 110 into sleeve 200, instead of pressurizing a container surrounding bag 110.

In some embodiments bag 110 is inserted full into sleeve 200. This process is optionally compatible with standard BIC filling procedures, and FIG. 15 shows a filled BIC bag 110 inserted into an expanded sleeve 200, after which sleeve 200 will be relaxed by withdrawal of arms 410, and the BIC/sleeve combination can be inserted into a standard BIC canister, or into any other package.

Some exemplary dimensions are as follows: in BOV technology currently in use, a rolled BOV ready for insertion in a sleeve is usually between about 12 mm and 18 mm in diameter, and often near 15 mm in diameter. In some embodiments sleeve 200 will be stretched to a diameter of between 20 and 25 mm, to accommodate the BOV. In an example of an embodiment of BIC technology currently in use, a pouch about 32 mm in diameter may be used, e.g. for a standard Shaving Gel canister. In some embodiments sleeve 200 will be stretched to a diameter of between 35 mm and 45 mm, for example about 40 mm, to allow insertion of the pouch. In any specific operational context a dimension for stretching of sleeve 200 will be selected taking into account the stretching mechanism used, a desired speed of operation, and other preferences and limitations.

Figure 16:
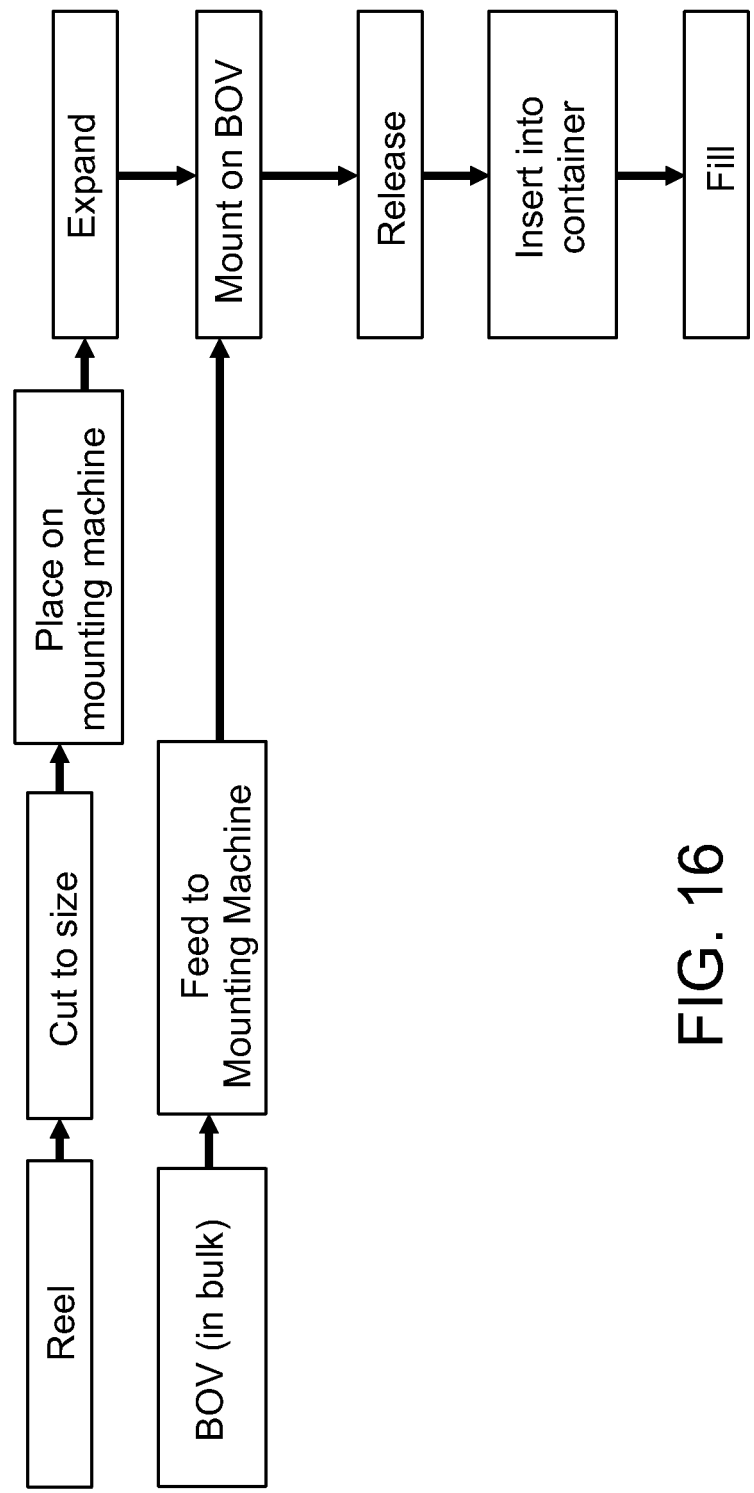
FIGS. 16 and 17 are simplified flow charts of processes for mass production of products, according to embodiments of the present invention.
Figure 17:
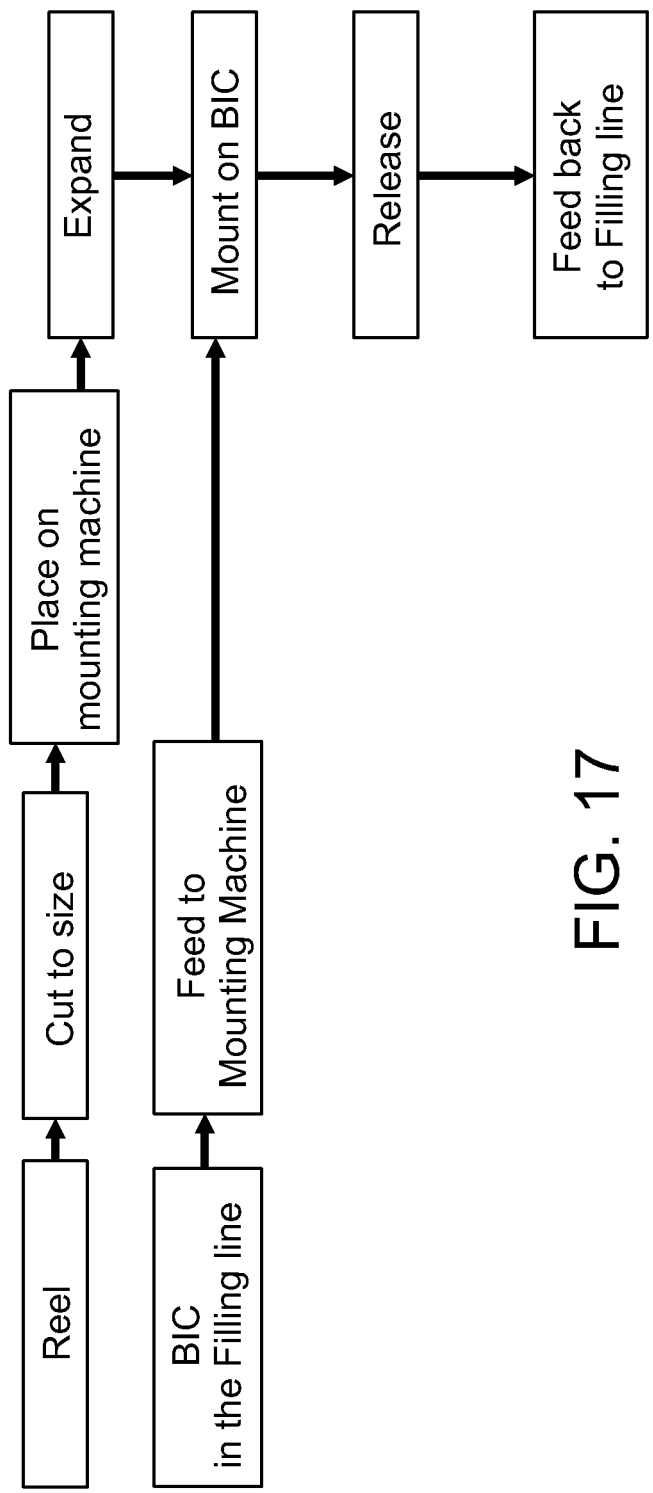

Attention is now drawn to FIGS. 16 and 17, which are simplified flow charts of processes for mass production of products incorporating embodiments of the present invention.

FIG. 16 shows a method for producing some BOV embodiments. As shown in the chart, extruded tubing from a reel is cut into appropriate lengths, placed on a mounting machine, and expanded, optionally using one of the expansion methods presented above. Empty and rolled BOV units from a supply of such units are fed to the mounting machine, which positions each BOV in an expanded sleeve 200, and allows the sleeve to contract. The BOV/sleeve combination, dispenser 100, is then inserted into a container, and the BOV bag 110 is filled with the material to be dispensed.

Note that to accomplish this process, in some embodiments minor modifications in a production line previously adapted to aerosol production according to methods of prior art may suffice to modify the line from producing products using a BOV compressed by a gas propellant, to producing products using a BOV compressed by a sleeve 200. Where a traditional process typically uses an inserting line to introduce a pre-prepared BOV into a pre-prepared can, introduce propellant, seal the can, fill material, test for leaks and weight, and package for shipment, an optional process according to an embodiment of the present invention comprises pre-preparing sleeves 200 (by extrusion and cutting to size) and mounting sleeves 200 on Bags, (optionally using one of the stretching procedures described above), thereby producing dispensers 100 (BOV+sleeve). At that point the BOVs with their sleeves can be handled in a manner similar to that used traditionally, but simplified. The BOVs prepared according to an embodiment of the present invent can be moved to BOV position in normal or slightly modified production machinery, where it is inserted in a container in a procedure which differs little (if at all) from prior art procedures for inserting a BOV into a container. The BOV may then be sealed into its container, either using prior art methods, materials and machinery (e.g. by crimping), or optionally using a simpler type of attachment, which is possible since a pressure-resistant seal is not needed. The prior art procedures for filling the container with propellant and testing for leaks may be skipped since they are not needed, and the product, now externally identical or very similar to a prior art product, is packaged for shipment. (Note also that shipping and handling can be simplified, since embodiments of the present invention, as contrasted to those of prior art, will not be considered a hazardous product requiring special handling.) In summary, sleeves 200 may be produced off line, and a standard production line may be used with only the addition of inserting BOV into sleeve before handling the BOV normally except for optionally using a simpler attachment method, and skipping because they are unnecessary, the prior art steps of insertion of propellant and testing for leaks.

FIG. 17 shows an optional method for producing BIC embodiments. As shown in the chart, extruded tubing from a reel is cut into appropriate lengths to produce sleeves 200, which sleeves are placed on a mounting machine, and expanded, optionally using one of the expansion methods presented above. FIG. 17 shows a process by which BIC bags filled on a filling line may be taken from the filling line, inserted in a sleeve 200, returned to the filling line, and thereafter be treated normally, i.e. according to the methods and optionally using the machines of prior art, except for skipping the production stages of filling with propellant and testing for leaks, pack and handle as is usual in the industry.

Attention is drawn to the fact that embodiments of the present invention may in some ways be safer than devices of prior art which use gas propellants. Dispensers with propellants may explode if overheated (left in a car in the sun, for example) because as their temperature goes up their internal pressure increases. If such a canister is punctured or otherwise fails, its contents may be likely to disperse under pressure. In contrast, with respect to embodiments deriving pressure from a sleeve 200 compressing a bag of materials, in the case of puncture or rupture of the sleeve, the pressurization of the bag contents may be reduced or eliminated when the sleeve fails, without the bag contents necessarily being dispersed, and should such an embodiment be heated, the rubber of the sleeve could become softer, probably resulting in a reduction of its internal pressure rather than an increase.

It is expected that during the life of a patent maturing from this application many relevant elastic materials will be developed and the scope of the term "sleeve" is intended to include all such new materials a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device for dispensing a material under pressure, comprising:

a) a flexible bag for containing said material and a valve assembly operable to control exit of said material from said bag; and b) an elastic compressing device which comprises a lumen having an open end, said compressing device containing said bag within said lumen with said open end surround a portion of said valve assembly;

wherein said compressing device is mounted on said valve assembly to allow movement of said open end of the compressing device with respect to the valve assembly.

2. The device of claim 1, comprising a mechanism which converts said material to an aerosol in air.

3. The device of claim 1, wherein said compressing device is constructed of an elastic material which comprises nanoparticles.

4. The device of claim 1, wherein said compressing device comprises a plurality of layers at least some of which have differing physical characteristics.

5. The device of claim 1, wherein said compressing device comprises a plurality of regions having differing physical characteristics.

6. The device of claim 1, further comprising an external container which contains said bag and said compressing device, and wherein a bottom of said bag is supported by a bottom of said external container.

7. The device of claim 1, further comprising non-cylindrical external container which contains said bag and said compressing device.

8. The device of claim 1, wherein an average thickness of wall of said compressing device is at most 3 mm before stretching.

9. A method for creating a pressurized dispenser for a fluidly dispensable material, comprising:
   a) providing a flexible bag having a valve assembly to control exit of said material from said flexible bag and an elastic compressing device with open first and second ends and a lumen extending from end to end;
   b) filling said flexible bag with said material;
   c) causing said compressing device to expand elastically in a manner which increases diameter of said lumen;
   d) inserting said filled bag into said expanded compressing device;
   e) relaxing said elastic expansion of said compressing device so that it contracts onto and pressurizes said bag and its contents
   f) mounting said compressing device to said valve assembly with said first open end of said compressing device surrounding at least a portion of said valve assembly to allow movement of said first open end of the compressing device with respect to the valve assembly.

10. A method for constructing pressurized dispensers of fluidly dispensable materials, comprising:
   a) using a mechanical tool to forcibly expand an elastic compressing device;
   b) inserting into a lumen of said expanded compressing device a flexible bag which connects to a valve assembly;
   c) relaxing said mechanical expansion, thereby allowing said compressing device to apply pressure to said bag, and subsequently filling said pressurized bag with said material; and
   d) mounting said compressing device to said valve assembly with an open end of said lumen surrounding at least a portion of said valve assembly to allow movement of said open end of the lumen with respect to the valve assembly.

11. A transfusion device operable to supply a liquid for transfusion into the bloodstream of a patient, comprising:
   a bag containing said liquid; and
   an elastic compressing device compressing said bag;
   wherein said bag is empty except for said liquid;
   wherein said bag is anchored to said compressing device at most by compressive forces exerted by said compressing device said bag.

12. A method for modifying a production line for aerosol products to produce aerosol products without gas propellants, comprising:
   a) providing equipment for mounting a compression device having a lumen and an open end on a valve assembly to allow movement of said open end with respect to said valve assembly, with said open end surrounding a portion of said valve assembly, said valve assembly controlling exit of a dispensable material from a bag, said compression device enclosing said bag to compress said bag to aerosol pressures;
   b) modifying product assembly equipment to insert said compressing device-enclosed bags instead of bags without compressing devices in an aerosol product's external container; and
   c) modifying said product assembly equipment so that it does not introduce a propellant into said external container.

13. A method for producing a product which dispenses a material under pressure, comprising:
   a) providing a bag for holding said material connected to a valve assembly for controlling passage of said material from said bag;
   said bag being enclosed in a lumen of a compressing device which compresses said bag;
   b) filling at least partially said bag with said material, thereby causing stretching of said compressing device; and
   c) mounting said compressing device to said valve assembly with an open end of said lumen surrounding at least a portion of said valve assembly to allow movement of said open end with respect to the valve assembly.

14. The device of claim 1, wherein said material is at least one of a group consisting of:
   a cosmetic cream;
   a cosmetic foam;
   a household cleaning agent;
   a shoe care product;
   a paint;
   a varnish;
   an air freshener;
   a deodorant;
   and anti-persperant;
   a hair spray;
   a hair mousse;
   a hair lacquer;
   a shaving gel;
   a shaving mousse;
   a sun-care spray;
   a medical treatment;
   a fire extinguisher; and
   a food.

15. The device of claim 1, wherein said pressure on said bag when said bag is empty is between 2 bar and 4 bar.

16. The device of claim 1, wherein said compression device is sized and shaped to apply a compressive force pressurizes a contents of said bag to a pressure of at least 6 bar when said bag is filled with said material.

17. The device of claim 1, wherein a portion of said compressing device adjacent to said open end has a funnel like form when said bag is filled with said material.

18. The method of claim 12, further comprising:
   providing filing equipment configured for filling said bag until said compression device applies at least six bar of pressure on said bag.

19. The method of claim 13 further comprising
   d) forming a portion of said compression device adjacent to said opening into a funnel shape during said filling.

20. The method of claim 13 wherein said providing includes:
   cutting said compression device from a continuous roll of extruded sleeve material and
   inserting said bag into said compression device.

21. The method of claim 13 wherein said providing includes:
   molding said compression device into a sleeve and
   inserting said bag into said compression device.

22. The method of claim 13 said compressing device is anchored to said valve assembly by compressive forces only.

23. The method of claim 13, wherein said filling is until said compression device applies at least six bar of pressure on said bag.

24. The method of claim 13, wherein said compressing device comprises a plurality of graspable shapes on its external surface and said method further comprises expanding said compressing device by grasping said graspable shapes and pulling said shapes away from each other.

25. A device for dispensing a material under pressure, comprising:
   a) a flexible bag for containing said material and a valve assembly positioned at a top extremity of said bag and operable to control exit of said material from said bag; and
   b) a compressive sleeve of elastomer strengthened with nano-particles which comprises a lumen, said sleeve containing said bag within said lumen;
   said sleeve and said bag being sized and positioned so that elastic contraction forces of said sleeve exert compressive pressure of at least 4 bar on said bag when said bag is filled with said material.

* * * * *